United States Patent [19]

Ueda et al.

[11] Patent Number: 4,742,057
[45] Date of Patent: May 3, 1988

[54] ANTIALLERGIC THIAZOLE COMPOUNDS

[75] Inventors: Ikuo Ueda; Masaaki Matsuo, both of Toyonaka; Takashi Manabe, Osaka; Hiroshi Matsuda, Kyoto, all of Japan

[73] Assignee: Fujisawa Pharmaceutical Co., Ltd., Osaka, Japan

[21] Appl. No.: 932,592

[22] Filed: Nov. 20, 1986

[30] Foreign Application Priority Data

Dec. 5, 1985 [JP] Japan ................................. 60-274465
Oct. 3, 1986 [JP] Japan ................................. 61-236879

[51] Int. Cl.⁴ .................... A61K 31/535; C07D 417/14
[52] U.S. Cl. .......................... 514/235.2; 514/228.2; 514/253; 514/316; 514/318; 514/323; 514/339; 544/58.6; 544/130; 544/131; 544/364; 546/187; 546/193; 546/194; 546/201; 546/273
[58] Field of Search ............. 546/201, 194, 187, 273, 546/193; 544/130, 131, 58.6, 364; 514/222, 231, 253, 316, 323, 318, 339

[56] References Cited

U.S. PATENT DOCUMENTS

| | | |
|---|---|---|
| 3,850,938 | 11/1974 | Derible et al. .................... 546/201 |
| 3,873,559 | 3/1975 | Narayanan et al. ............ 546/201 X |
| 3,980,658 | 9/1976 | Possanza et al. .................... 546/201 |
| 3,993,764 | 11/1976 | Dumont et al. .................... 514/323 |
| 4,100,291 | 7/1978 | Clemence et al. .................. 546/201 |
| 4,195,081 | 3/1980 | Nedelec et al. .................... 514/339 |
| 4,196,209 | 4/1980 | Dumont et al. .................... 546/201 |
| 4,278,677 | 7/1981 | Nedelec et al. ................. 546/273 X |
| 4,324,790 | 4/1982 | Guillaume et al. ............. 546/273 X |
| 4,359,468 | 11/1982 | Freter et al. .................. 546/199 X |
| 4,530,932 | 7/1985 | Clemence et al. .................. 514/318 |
| 4,548,939 | 10/1985 | Kennis et al. ................. 546/201 X |

FOREIGN PATENT DOCUMENTS 0200322 11/1986 European Pat. Off. ............ 546/201

OTHER PUBLICATIONS

D. Beck, et al., *Helv. Chim. Acta,* 51, 260-264 (1968).

*Primary Examiner*—Richard A. Schwartz
*Attorney, Agent, or Firm*—Oblon, Fisher, Spivak, McClelland & Maier

[57] ABSTRACT

A thiazole compound of allergically activity of the formula:

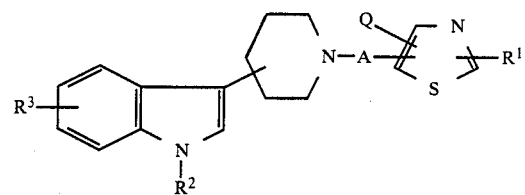

wherein
$R^1$ is amino optionally having suitable substituent(s),
$R^2$ is hydrogen, lower alkyl or aryl,
$R^3$ is hydrogen, nitro, amino optionally having suitable substituent(s), hydroxy or lower alkoxy,
A is lower alkylene,
Q is hydrogen or halogen, and
a heavy solid line means a single or double bond, or a pharmaceutically acceptable salt thereof, processes for the preparation thereof and pharmaceutical composition comprising the same.

14 Claims, No Drawings

ANTIALLERGIC THIAZOLE COMPOUNDS

This invention relates to new thiazole compounds and pharmaceutically acceptable salts thereof.

More particularly, it relates to new thiazole compounds and pharmaceutically acceptable salts thereof which have antiallergic activity, to processes for the preparation thereof, to a pharmaceutical composition comprising the same and to a method for the treatment of allergic disease in human being or animals.

One object of this invention is to provide new thiazole compounds and pharmaceutically acceptable salts thereof which possess antiallergic activity.

Another object of this invention is to provide processes for the preparation of said thiazole compounds or salts thereof.

A further object of this invention is to provide a pharmaceutical composition comprising, as an active ingredient, said thiazole compounds or pharmaceutically acceptable salts thereof.

Still further object of this invention is to provide a therapeutical method for the treatment of allergic disease such as allergic asthma, allergic rhinitis, allergic conjunctivitis, chronic urticaria, or the like, in human being or animals.

Some indolylpiperidine compounds having antiallergic activity have been known as described in British Patent Application Publication No. 2093455.

The object thiazole compounds of this invention are new and can be represented by the following general formula [I]:

wherein
R$^1$ is amino optionally having suitable substituent(s),
R$^2$ is hydrogen, lower alkyl or aryl,
R$^3$ is hydrogen, nitro, amino optionally having suitable substituent(s), hydroxy or lower alkoxy,
A is lower alkylene,
Q is hydrogen or halogen, and
a heavy solid line means a single or double bond.

In case that the aminothiazole moiety of the object compound [I] is 2-optionally mono-substituted aminothiazole, it may also exist as 2-optionally substituted imino-thiazoline, which is a tautomer of aminothiazole as follows:

wherein
R$^{1'}$ is amino optionally having one suitable substituent,
R$^{1''}$ is imino optionally having a suitable substituent, and
Q is as defined above.

Both of the above tautomeric isomers are included within the scope of the present invention, and in the present specification and claims, however, they are represented as 2-optionally mono-substituted aminothiazole for the convenient sake.

The object compound [I] or its salt can be prepared by processes as illustrated in the following reaction schemes.

Process 1

Process 2

Process 3

-continued
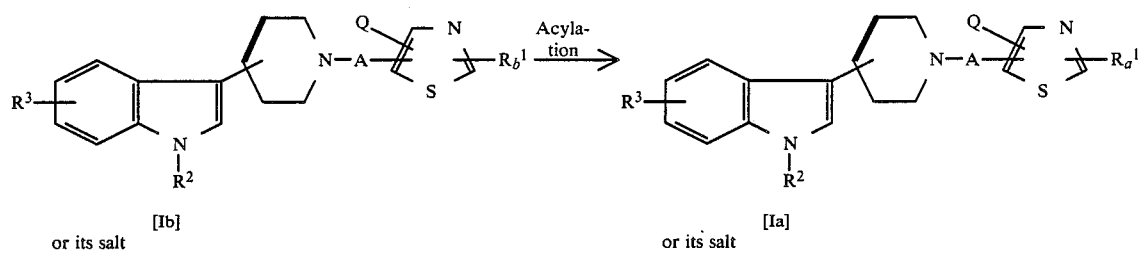
[Ib] or its salt → [Ia] or its salt
Process 4
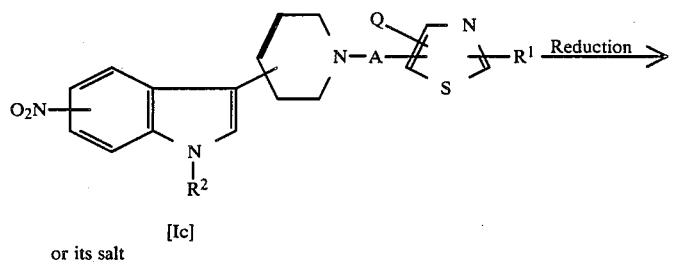
[Ic] or its salt
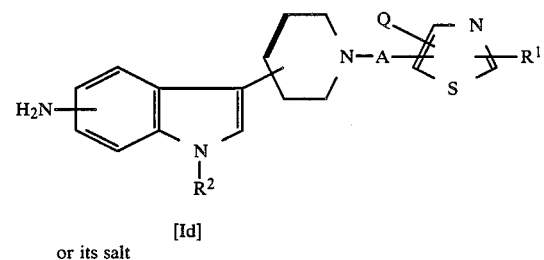
[Id] or its salt
Process 5
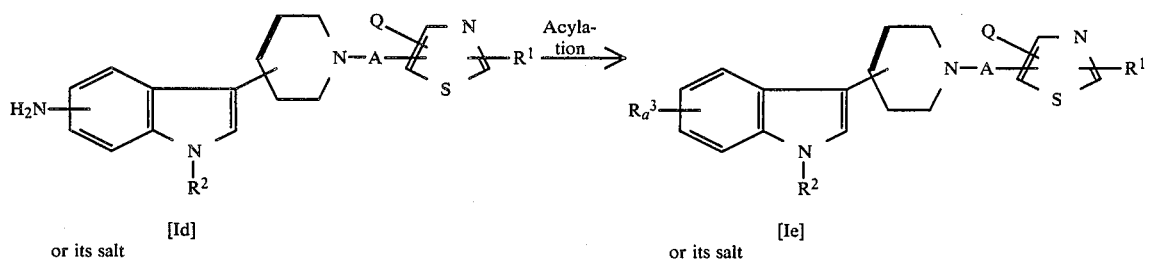
[Id] or its salt → [Ie] or its salt
Process 6
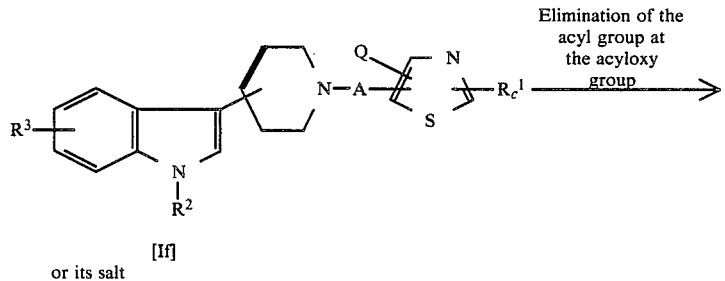
[If] or its salt -continued

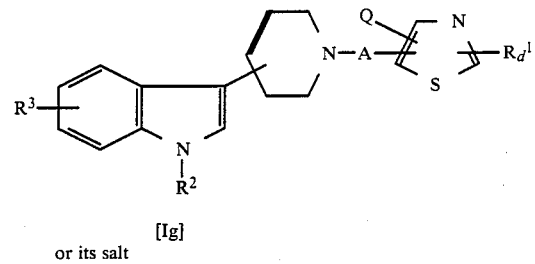

[Ig]
or its salt

Process 7

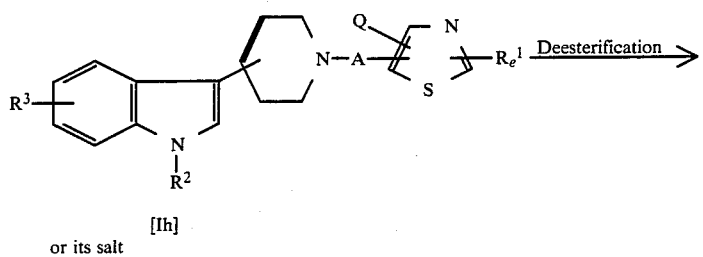 Deesterification →

[Ih]
or its salt

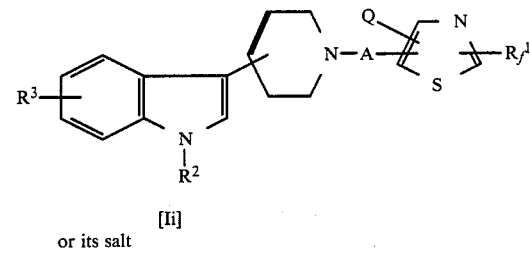

[Ii]
or its salt

Process 8

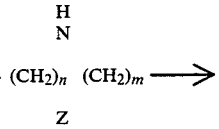
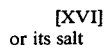

[Ij]
or its salt

[XVI]
or its salt

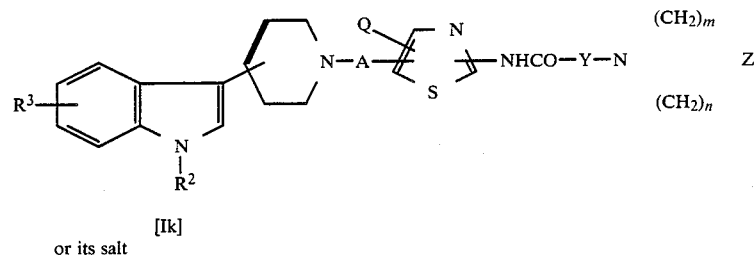
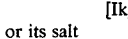

[Ik]
or its salt wherein
 $R_a^1$ is acylamino, N,N-diacylamino or N-acyl-N-(lower) alkylamino,
 $R_b^1$ is amino or lower alkylamino,
 $R_c^1$ is acylamino substituted with acyloxy,
 $R_d^1$ is acylamino substituted with hydroxy,
 $R_e^1$ is acylamino substituted with esterified carboxy,
 $R_f^1$ is acylamino substituted with carboxy,
 $R_a^3$ is acylamino,
 $R^5$ is lower alkenyl,
 X is a leaving group,
 Y is lower alkylene,
 Z is O, S, NH or a single bond,
 m is an integer of 1, 2 or 3,
 n is an integer of 0, 1, 2 or 3, and
 $R^1$, $R^2$, $R^3$, A, Q and a heavy solid line are each as defined above.

In the above and subsequent descriptions of the present specification, suitable examples of the various definitions to be included within the scope of the invention are explained in detail in the following.

The term "lower" is intended to mean a group having 1 to 6 carbon atom(s), unless otherwise provided.

The term "higher" is intended to mean a group having 7 to 20 carbon atoms, unless otherwise provided.

Suitable "lower alkyl" may be a straight or branched one such as methyl, ethyl, propyl, isopropyl, butyl, isobutyl, tert-butyl, pentyl, hexyl or the like, in which the preferable one is $C_1-C_4$ alkyl and the most preferable one is methyl or ethyl.

Suitable "lower alkenyl" may be vinyl, allyl, propenyl, isopropenyl, butenyl, pentenyl or the like, in which the preferable one is $C_2-C_4$ alkenyl and the most preferable one is vinyl or allyl.

Suitable "aryl" may be phenyl, naphthyl, tolyl, mesityl, cumenyl or the like, in which the preferable one is phenyl.

Suitable "lower alkoxy" may be a straight or branched one such as methoxy, ethoxy, propoxy, isopropoxy, butoxy, isobutoxy, tert-butoxy, pentyloxy, hexyloxy or the like, in which the preferable one is $C_1-C_4$ alkoxy and the most preferable one is methoxy or ethoxy.

Suitable "lower alkylene" may be a straight or branched one such as methylene, ethylene, trimethylene, methylethylene, tetramethylene, ethylethylene, propylene, pentamethylene, hexamethylene or the like.

Suitable "halogen" is fluorine, chlorine, bromine and iodine.

Suitable "acyl" and acyl moiety in the terms "acylamino", "N,N-diacylamino", "N-acyl-N-(lower)alkylamino" and "acyloxy" may be alkanoyl such as straight or branched lower alkanoyl [e.g. formyl, acetyl, propionyl, butyryl, isobutyryl, valeryl, isovaleryl, pivaloyl, hexanoyl, 3,3-dimethylbutyryl, etc.] or higher alkanoyl [e.g. heptanoyl, octanoyl, myristoyl, palmitoyl, stearoyl, etc.], straight or branched lower alkenoyl [e.g. acryloyl, crotonoyl, isocrotonoyl, 3-butenoyl, methacryloyl, etc.], lower alkynoyl [e.g. propioloyl, 2-butynoyl, 3-butynoyl, etc.], mono- or di- or trihalo(lower)alkanoyl [e.g. chloroacetyl, trifluoroacetyl, etc.], cyclo(lower)alkylcarbonyl [e.g. cyclopropylcarbonyl, cyclobutylcarbonyl, cyclopentylcarbonyl, cyclohexylcarbonyl, etc.], cyclo(lower)alkenylcarbonyl [e.g. cyclopentenylcarbonyl, cyclohexenylcarbonyl, etc.], lower alkoxycarbonyl [e.g. methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, hexyloxycarbonyl, etc.], hydroxy(lower)alkanoyl [e.g. glycoloyl, lactoyl, 3-hydroxypropionyl, glyceroyl, etc.], lower alkoxy(lower)alkanoyl [e.g. methoxyacetyl, ethoxyacetyl, methoxypropionyl, ethoxypropionyl, propoxypropionyl, methoxybutyryl, etc.], lower alkanoyloxy(lower)alkanoyl [e.g. acetyloxyacetyl, acetyloxypropionyl, propionyloxyacetyl, etc.], carbamoyl, lower alkylcarbamoyl [e.g. methylcarbamoyl, ethylcarbamoyl, propylcarbamoyl, isopropylcarbamoyl, butylcarbamoyl, isobutylcarbamoyl, tert-butylcarbamoyl, etc.], amino substituted alkanoyl [e.g. glycyl, alanyl, β-alanyl, 4-aminobutyryl, 4-aminovaleryl, 5-aminovaleryl, leucyl, valyl, etc.], carboxy substituted lower alkanoyl [e.g. oxalo, carboxyacetyl, 3-carboxypropionyl, 3-carboxybutyryl, 4-carboxybutyryl, 4-carboxyvaleryl, etc.], lower alkoxycarbonylcarbonyl [e.g. methoxalyl, ethoxalyl, etc.], esterified carboxy(lower)alkanoyl, for example, lower alkoxycarbonyl(lower)alkanoyl [e.g. methoxycarbonylacetyl, ethoxycarbonylacetyl, methoxycarbonylpropionyl, ethoxycarbonylpropionyl, etc.], etc., lower alkanoylcarbonyl [e.g. glyoxyloyl, pyruvoyl, etc.], lower alkanoyl(lower)alkanoyl [e.g. acetoacetyl, acetopropionyl, etc.], amino and carboxy substituted alkanoyl [e.g. α-aspartyl, β-aspartyl, α-glutamyl, γ-glutamyl, etc.], aroyl [e.g. benzoyl, toluoyl, xyloyl, naphthoyl, etc.], heterocyclic carbonyl [e.g. furoyl, thenoyl, nicotinoyl, isonicotinoyl, etc.], aralkanoyl [e.g. phenylacetyl, tolylacetyl, naphthylacetyl, 2-phenylpropionyl, 3-phenylpropionyl, 4-phenylbutyryl, tritylcarbonyl, etc.], aralkenoyl [e.g. cinnamoyl, etc.], heterocyclic(lower)alkanoyl [e.g. morpholinoacetyl, morpholinopropionyl, thiomorpholinopropionyl, piperidinopropionyl, piperazinylpropionyl, pyrrolidinylpropionyl, imidazolidinylpropionyl, etc.], lower alkylsulfonyl [e.g. mesyl, ethylsulfonyl, propylsulfonyl, isopropylsulfonyl, tert-butylsulfonyl, pentylsulfonyl, etc.], arylsulfonyl [e.g. tosyl, phenylsulfonyl, etc.], or the like.

Suitable substituent in the terms "amino optionally having suitable substituent(s)" and "amino optionally having one suitable substituent" may include the above-mentioned lower alkyl, the above-mentioned lower alkenyl, lower alkynyl [e.g. ethynyl, propynyl, butynyl, etc.], the above-mentioned acyl, the abovementioned aryl and the like.

Preferable examples of "amino optionally having suitable substituent(s)" may include amino, mono- or disubstituted amino such as lower alkylamino [e.g. methylamino, ethylamino, propylamino, isobutylamino, etc.], lower alkenylamino[e.g. vinylamino, allylamino, etc.], lower alkynylamino[e.g. ethynylamino, etc.], acylamino, for example, lower alkanoylamino [e.g. formylamino, acetylamino, propionylamino, butyrylamino, isobutyrylamino, valerylamino, isovalerylamino, pivaloylamino, hexanoylamino, 3,3-dimethylbutyrylamino, etc.], higher alkanoylamino [e.g. heptanoylamino, octanoylamino, stearoylamino, etc.], lower alkenoylamino [e.g. acryloylamino, crotonoylamino, isocrotonoylamino, etc.], lower alkynoylamino [e.g. propioloylamino, etc.], mono- or di- or trihalo(lower)alkanoylamino [e.g. chloroacetylamino, trifluoroacetylamino, etc.], cyclo(lower)alkylcarbonylamino [e.g. cyclopropylcarbonylamino, cyclobutylcarbonylamino, cyclopentylcarbonylamino, etc.], cyclo(lower)alkenylcarbonylamino [e.g. cyclopentenylcarbonylamino, etc.], lower alkoxycarbonylamino [e.g. methoxycarbonylamino, ethoxycarbonylamino, propoxycarbonylamino, etc.], hydroxy(lower)alkanoylamino [e.g. glycoloylamino, lactoylamino, 3-hydroxypropionylamino, glyceroylamino, etc.], lower alkoxy(lower)alkanoylamino [e.g. methoxyacetylamino, methoxypropionylamino, etc.], lower alkanoyloxy(lower)alkanoylamino [e.g. acetyloxyacetylamino, acetyloxypropionylamino, etc.], ureido, lower alkylureido [e.g. methylureido, ethylureido, etc.], amino substituted alkanoylamino [e.g. glycylamino, alanylamino, β-alanylamino, etc.], carboxy substituted lower alkanoylamino [e.g. oxaloamino, carboxyacetylamino, 3-carboxypropionylamino, etc.], lower alkoxycarbonylcarbonylamino [e.g. methoxalylamino, ethoxalylamino, etc.], esterified carboxy(lower)alkanoylamino [e.g. lower alkoxycarbonyl(lower)alkanoylamino, (e.g. methoxycarbonylacetylamino, methoxycarbonylpropionylamino, etc.) etc.], lower alkanoylcarbonylamino [e.g. glyoxyloylamino, pyruvoylamino, etc.], lower alkanoyl(lower)alkanoylamino [e.g. acetoacetylamino, etc.], amino and carboxy substituted alkanoylamino [e.g. α-aspartylamino, β-aspartylamino, α-glutamylamino, γ-glutamylamino, etc.], aroylamino [e.g. benzoylamino, toluoylamino, etc.], heterocyclic carbonylamino [e.g. nicotinoylamino, etc.], aralkanoylamino [e.g. phenylacetylamino, etc.], aralkenoylamino [e.g. cinnamoylamino, etc.], heterocyclic(lower)alkanoylamino [e.g. morpholinoacetylamino, morpholinopropionylamino, piperidinopropionylamino, etc.], lower alkylsulfonylamino [e.g. mesylamino, ethylsulfonylamino, propylsulfonylamino, isopropylsulfonylamino, tert-butylsulfonylamino, etc.], arylsulfonylamino [e.g. tosylamino, phenylsulfonylamino, etc.], and the like, arylamino [e.g. phenylamino, tolylamino, naphthylamino, etc.], N,N-diacylamino [e.g. N,N-di(lower)alkylsulfonylamino (e.g. N,N-dimesylamino, N,N-di(ethylsulfonyl)amino, etc.), etc.] and N-acyl-N-(lower)alkylamino [e.g. N-(lower)alkanoyl-N-(lower)alkylamino (e.g. N-acetyl-N-methylamino, N-propionyl-N-methylamino, N-propionyl-N-ethylamino, etc.), N-cyclo(lower)alkylcarbonyl-N-(lower)alkylamino (e.g. N-cyclopropylcarbonyl-N-methylamino, N-cyclopropylcarbonyl-N-ethylamino, N-cyclobutylcarbonyl-N-methylamino, etc.), N-(lower)alkylsulfonyl-N-(lower)alkylamino (e.g. N-mesyl-N-methylamino, N-ethylsulfonylamino-N-methylamino, N-mesyl-N-ethylamino, etc.), etc.].

Preferable examples of "optionally mono-substituted amino" and "amino optionally having one suitable substituent" are amino and the above-mentioned monosubstituted amino.

Preferable examples of "acylamino", "N,N-diacylamino", "N-acyl-N-(lower)alkylamino" and "lower alkylamino" can be referred to the ones as exemplified above.

Preferable examples of "acylamino substituted with acyloxy" may be the above-mentioned lower alkanoyloxy(lower)alkanoylamino, or the like.

Preferable examples of "acylamino substituted with hydroxy" may be the above-mentioned hydroxy(lower)alkanoylamino, or the like.

Preferable examples of "acylamino substituted with esterified carboxy" may be the above-mentioned lower alkoxycarbonyl(lower)alkanoylamino, or the like.

Preferable examples of "acylamino substituted with carboxy" may be the above-mentioned carboxy substituted lower alkanoylamino, or the like.

Preferable examples of the compound [XVI] may be morpholine, thiomorpholine, piperidine, piperazine, oxazolidine, isoxazolidine, thiazolidine, isothiazolidine, imidazolidine, pyrazolidine, pyrrolidine or the like.

Suitable "leaving group" may be an acid residue such as halogen [e.g. chlorine, bromine, fluorine and iodine], sulfonyloxy [e.g. mesyloxy, tosyloxy, phenylsulfonyloxy, etc.] or the like.

Suitable pharmaceutically acceptable salts of the object compound [I] are conventional non-toxic salts and include a metal salt such as an alkali metal salt [e.g. sodium salt, potassium salt, etc.] and an alkaline earth metal salt [e.g. calcium salt, magnesium salt, etc.], an ammonium salt, an organic base salt [e.g. trimethylamine salt, triethylamine salt, pyridine salt, picoline salt, dicyclohexylamine salt, N,N'-dibenzylethylenediamine salt, etc.], an organic acid addition salt [e.g. formate, acetate, trifluoroacetate, maleate, tartrate, methanesulfonate, benzenesulfonate, toluenesulfonate, etc.], an inorganic acid addition salt [e.g. hydrochloride, hydrobromide, sulfate, phosphate, etc.], a salt with an amino acid [e.g. arginine salt, aspartic acid salt, glutamic acid salt, etc.], an intramolecular salt and the like.

With respect to the salts of the compounds [Ia] to [Ik] in the Processes 1 to 8, it is to be noted that these compounds are included within the scope of the compound [I], and accordingly the suitable examples of the salts of these compounds are to be referred to those as exemplified for the object compound [I].

The processes for preparing the object compounds [I] of the present invention are explained in detail in the following.

Process 1

The object compound [I] or its salt can be prepared by reacting a compound [IV] or its salt with a compound [V] or its salt.

As suitable examples of the salts of the compounds [IV] and [V], there may be mentioned the same kinds of salt as given for the compound [I].

This reaction is usually carried out in a conventional solvent such as water, an alcohol [e.g. methanol, ethanol, isopropyl alcohol, etc.], dioxane, tetrahydrofuran, N,N-dimethylformamide, methylene chloride, chloroform, tetrachloromethane, or any other conventional solvent which does not adversely affect this reaction, or a mixture thereof.

The reaction is carried out at ambient temperature, under warming or under heating, although the reaction temperature is not critical.

This reaction can also be conducted in the presence of an inorganic base, for example an alkali metal hydroxide such as sodium hydroxide or potassium hydroxide, or an alkali metal carbonate or hydrogen carbonate such as sodium carbonate, potassium carbonate, sodium hydrogen carbonate or potassium hydrogen carbonate, or in the presence of an organic base, for example a tertiary amine such as triethylamine, pyridine or N,N-dimethylaniline.

This reaction can also be performed in the presence of an alkali metal halide such as sodium iodide or potassium iodide.

Process 2

The object compound [Ib] or its salt can be prepared by subjecting a compound [Ia] or its salt to solvolysis reaction.

This solvolysis reaction can be carried out in a similar manner to that of conventional hydrolysis or aminolysis.

The aminolysis can be conducted, for example by using hydrazine or ammonia in a conventional solvent such as water, an alcohol [e.g. methanol, ethanol, etc.], chloroform, methylene chloride, or the like.

The hydrolysis can be effected in the presence of an acid such as hydrochloric acid, sulfuric acid, acetic acid, trifluoroacetic acid or p-toluenesulfonic acid or a base such as sodium hydroxide or sodium ethoxide, in an alcohol as mentioned above, benzene, water or any other solvent which does not adversely affect this reaction.

The reaction temperature is not critical, and the reaction can be carried out under cooling, at ambient temperature or under heating.

Process 3

The object compound [Ia] or its salt can be prepared by reacting a compound [Ib] or its salt with an acylating agent.

Suitable acylating agents are the corresponding carboxylic acid or sulfonic acid compounds, which are represented by the formula: $R^6$-OH wherein $R^6$ is acyl, and reactive derivatives thereof, and the corresponding isocyanate compounds.

As suitable said reactive derivatives, there may be mentioned acid halides, acid anhydrides, active amides and active esters. Suitable examples are acid halides such as acid chloride and acid bromide, mixed acid anhydrides with various acids [e.g. substituted phosphoric acid such as dialkyl phosphoric acid, sulfuric acid, aliphatic carboxylic acid, aromatic carboxylic acid, etc.], symmetric acid anhydrides, active amides with various imidazoles, and active esters such as cyanomethyl ester, methoxymethyl ester, p-nitrophenyl ester, 2,4-dinitrophenyl ester, pentachlorophenyl ester, phenylazophenyl ester, carboxymethylthio ester and N-hydroxysuccinimide ester. The kind of such reactive derivatives can be selected depending on the kind of acyl group to be introduced.

The reaction is usually carried out in a conventional solvent, such as methylene chloride, chloroform, benzene, toluene, pyridine, diethyl ether, dioxane, tetrahydrofuran, acetone, acetonitrile, ethyl acetate, N,N-dimethylformamide or any other organic solvent which does not adversely affect the reaction. In case that the acylating agent is liquid, it can also be used as a solvent. In case that the carboxylic acid or sulfonic acid compounds are used as acylating agent in the free acid form or salt form, it is preferable to carry out the reaction in the presence of a conventional condensing agent such as N,N'-dicyclohexylcarbodiimide or the like.

The reaction temperature is not critical and the reaction can be carried out under cooling, at ambient temperature, or under heating.

This reaction is preferably carried out in the presence of an inorganic base, for example an alkali metal hydroxide such as sodium hydroxide or potassium hydroxide, or an alkali metal carbonate or hydrogen carbonate such as sodium carbonate, potassium carbonate, sodium hydrogen carbonate or potassium hydrogen carbonate, or in the presence of an organic base, for example a tertiary amine such as triethylamine, pyridine or N,N-dimethylaniline.

In certain reaction condition, in case that the starting compound of the formula:

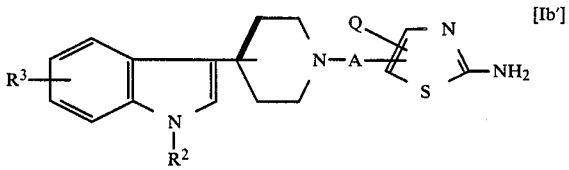

[Ib']

wherein $R^2$, $R^3$, A, Q and a heavy solid line are each as defined above, is used, the 2-acylimino-3-acylthiazoline compound of the formula:

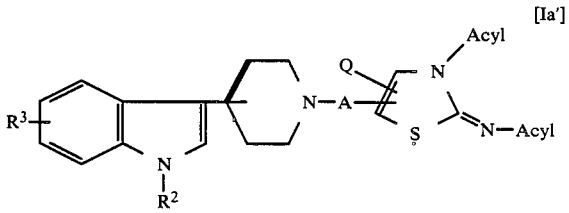

[Ia']

wherein
Acyl is acyl, and $R^2$, $R^3$, A, Q and a heavy solid line are each as defined above, may be obtained as by-product. In such case, the compound [Ia] can be easily prepared by subjecting said compound [Ia'] to conventional hydrolysis reaction, which is also included within the scope of the present process.

Process 4

The object compound [Id] or its salt can be prepared by reducing a compound [Ic] or its salt.

The reduction can be carried out in a conventional manner, namely, chemical reduction or catalytic reduction.

Suitable reducing agents to be used in chemical reduction may be a combination of metal [e.g. tin, zinc, iron, etc.] and ammonium chloride or an base [e.g. ammonia, sodium hydroxide, etc.], a combination of the above-mentioned metal or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.], alkali metal borohydride [e.g. lithium borohydride, sodium borohydride, potassium borohydride etc.], alkali metal cyanoborohydride [e.g. sodium cyanoborohydride, etc.] or alkali metal aluminum hydride [e.g. lithium aluminum hydride, etc.] or the like.

Suitable catalysts to be used in catalytic reduction are conventional ones such as platinum catalyst [e.g. platinum plate, spongy platinum, platinum black, colloidal platinum, platinum oxide, platinum wire, etc.], palladium catalyst [e.g. spongy palladium, palladium black, palladium oxide, palladium on carbon, colloidal palladium, palladium on barium sulfate, palladium on barium carbonate, etc.], nickel catalyst [e.g. reduced nickel, nickel oxide, Raney nickel, etc.], cobalt catalyst [e.g. reduced cobalt, Raney cobalt, etc.], iron catalyst [e.g. reduced iron, Raney iron, etc.], copper catalyst [e.g. reduced copper, Raney copper, Ullman copper, etc.] or the like.

The reaction of this process is usually carried out in a solvent such as water, alcohol [e.g. methanol, ethanol, propanol, etc.], acetic acid, diethyl ether, dioxane, tetrahydrofuran, etc. or a mixture thereof.

The reaction is usually carried out under cooling to warming or heating.

Process 5

The object compound [Ie] or its salt can be prepared by reacting a compound [Id] or its salt with an acylating agent.

This reaction can be carried out in substantially the same manner as that of Process 3, and therefore the reaction mode and reaction conditions of this reaction can be referred to those as explained in Process 3.

Process 6

The object compound [Ig] or its salt can be prepared by subjecting a compound [If] or its salt to elimination reaction of the acyl group at the acyloxy group.

This reaction can be carried out in substantially the same manner as hydrolysis explained in Process 2, and therefore the reaction mode and reaction conditions of this reaction can be referred to those of hydrolysis as explained in Process 2.

Process 7

The object compound [Ii] or its salt can be prepared by subjecting a compound [Ih] or its salt to deesterification reaction.

The present deesterification reaction may include conventional deesterification reaction such as hydrolysis, reduction or the like.

This reaction can be preferably carried out in substantially the same manner as hydrolysis explained in Process 2, and therefore the reaction mode and reaction conditions of this reaction can be referred to those of hydrolysis as explained in Process 2.

Process 8

The object compound [Ik] or its salt can be prepared by reacting a compound [Ij] or its salt with a compound [XVI] or its salt.

As suitable examples of the salt of the compound [XVI], there may be mentioned the acid addition salt as given for the compound [I].

This reaction is usually carried out in a conventional solvent such as water, alcohol [e.g. methanol, ethanol, etc.], dioxane, tetrahydrofuran, N,N-dimethylformamide, methylene chloride, chloroform, tetrachloromethane or any other organic solvent which does not adversely affect the reaction. In case that the compound [XVI] is liquid, it can also be used as a solvent.

The reaction temperature is not critical, and the reaction is usually carried out under warming to heating.

Among the starting compounds [IV] and [V] in the Process 1, some of them are new and such compounds can be prepared by processes as illustrated in the following reaction schemes.

Process A

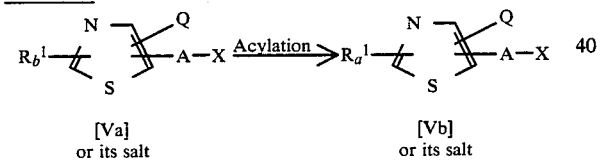

[Va] or its salt → [Vb] or its salt

Process B

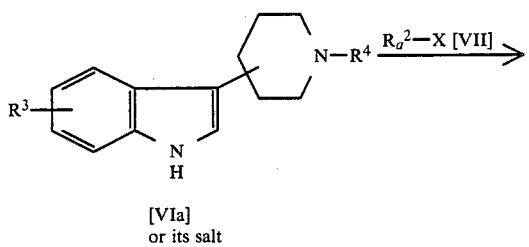

[VIa] or its salt

[VIb] or its salt

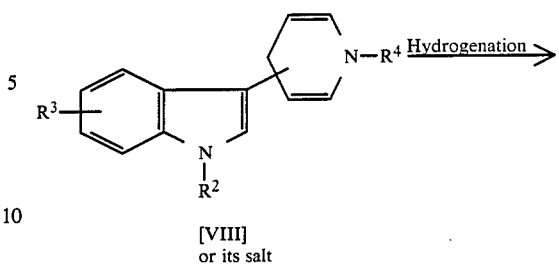

[VIII] or its salt

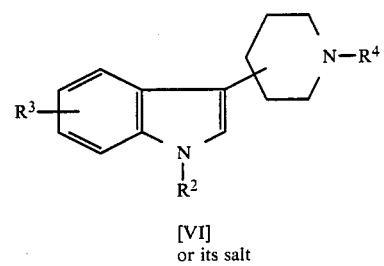

[VI] or its salt

Process D

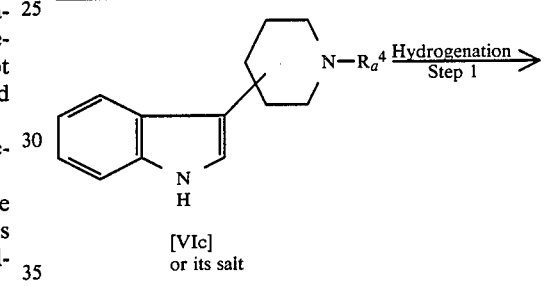

[VIc] or its salt

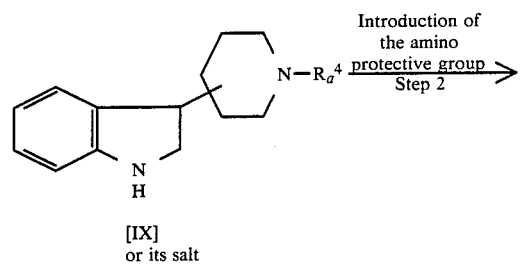

[IX] or its salt

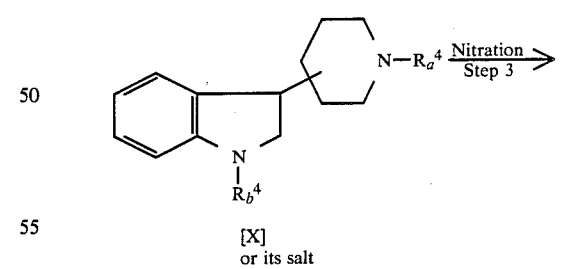

[X] or its salt

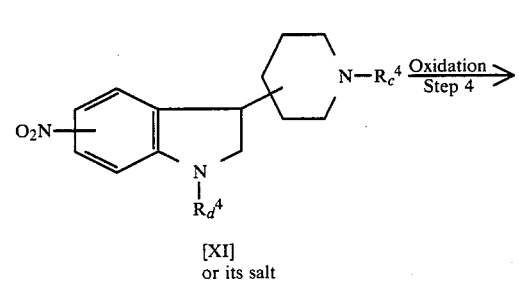

[XI] or its salt

Process C

15

-continued

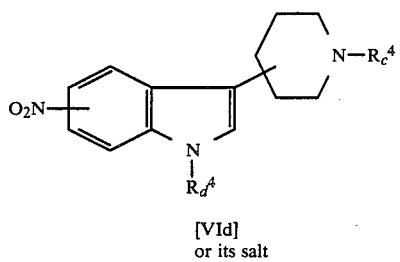

[VId] or its salt

Process E

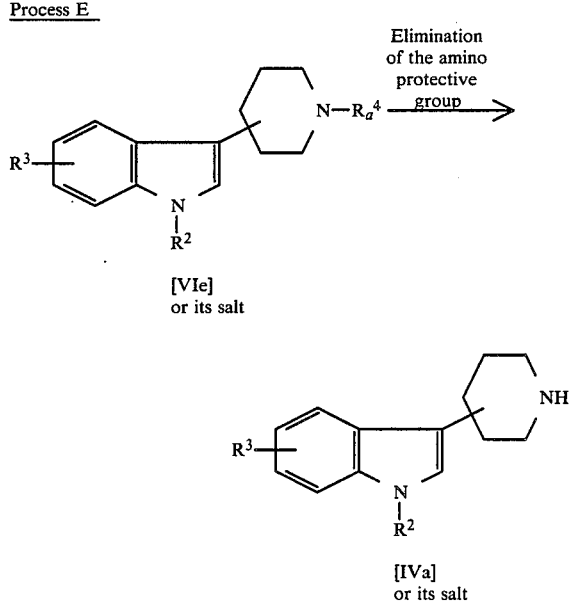

wherein
R[4] is hydrogen or an amino protective group,
$R_a{}^2$ is aryl,
$R_a{}^4$ and $R_b{}^4$ are each an amino protective group,
$R_c{}^4$ and $R_d{}^4$ each hydrogen or an aminoprotective group, and
$R^2$, $R^3$, $R_a{}^1$, $R_b{}^1$, A, Q and X are each as defined above.

Suitable "amino protective group" may be a group, which can be easily introduced or eliminated, such as acyl, for example, substituted or unsubstituted lower alkanoyl [e.g. formyl, acetyl, propionyl, trifluoroacetyl, etc.], lower alkoxycarbonyl [e.g. tertbutoxycarbonyl, etc.], substituted or unsubstituted aralkyloxycarbonyl [e.g. benzyloxycarbonyl, p-nitrobenzyloxycarbonyl, etc.] or the like, aralkyl [e.g. trityl, benzyl, etc.] or the like.

The processes for preparing the starting compounds are explained in detail in the following.

Process A

The compound [Vb] or its salt can be prepared by reacting a compound [Va] or its salt with an acylating agent.

As suitable examples of the salts of the compounds [Va] and [Vb], there may be mentioned the same kinds of salt as given for the compound [I].

This reaction can be carried out in substantially the same manner as that of Process 3, and therefore the reaction mode and reaction conditions of this reaction can be referred to those as explained in Process 3.

16

In certain reaction condition, in case that the starting compound of the formula:

[Va']

wherein A, Q and X are each as defined above, is used, the 2-acylimino-3-acylthiazoline compound of the formula:

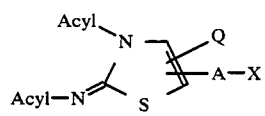

[Vb']

wherein A, Q, X and Acyl are each as defined above, may be obtained as by-product. In such case, the compound [Vb] can be easily prepared by subjecting said compound [Vb'] to conventional hydrolysis reaction, which is also included within the scope of the present process.

Process B

The compound [VIb] or its salt can be prepared by reacting a compound [VIa] or its salt with a compound [VII].

As suitable examples of the salts of the compounds [VIa] and [VIb], there may be mentioned the same kinds of salt as given for the compound [I].

This reaction is preferably carried out in the presence of a base such as an inorganic base, for example alkali metal hydroxide [e.g. sodium hydroxide, potassium hydroxide, etc.] or alkali metal carbonate or bicarbonate [e.g. sodium carbonate, potassium carbonate, sodium bicarbonate, potassium bicarbonate, etc.], or an organic base, for example tertiary amines [e.g. triethylamine, pyridine, N,N-dimethylaniline, etc.].

This reaction is usually carried out in the presence of a catalyst such as copper powder, copper halide [e.g. copper (I) chloride, copper (I) bromide, copper (I) iodide, etc.], copper oxide [e.g. copper (II) oxide, etc.], iron halide [e.g. iron (II) chloride, etc.] or the like.

This reaction is usually carried out in a conventional solvent such as water, alcohol [e.g. methanol, ethanol, isopropyl alcohol, etc.], dioxane, tetrahydrofuran, N,N-dimethylformamide, methylene chloride, chloroform, tetrachloromethane, or any other organic solvent which does not adversely influence the reaction.

The reaction temperature is not critical and the reaction is usually carried out at ambient temperature, under warming or under heating.

Process C

The compound [VI] or its salt can be prepared by hydrogenating a compound [VIII] or its salt.

As suitable examples of the salts of the compounds [VI] and [VIII], there may be mentioned the same kinds of salt as given for the compound [I].

The reaction can be carried out in a conventional manner, namely, chemical reduction or catalytic reduction.

Suitable reducing agents to be used in chemical reduction are a metal hydride compound such as aluminum hydride compound [e.g. lithium aluminum hydride, sodium aluminum hydride, aluminum hydride, lithium trimethoxyaluminum hydride, lithium tri-tert-butoxyaluminum hydride, etc.], borohydride compound [e.g. sodium borohydride, lithium borohydride, sodium cyanoborohydride, tetramethylammonium borohydride, etc.], borane, diborane or the like.

Suitable catalysts to be used in catalytic reduction are conventional ones such as platinum catalyst [e.g. platinum plate, spongy platinum, platinum black, colloidal platinum, platinum oxide (so-called Adams catalyst), platinum wire, etc.], palladium catalyst [e.g. spongy palladium, palladium black, palladium oxide, palladium on carbon, colloidal palladium, palladium on barium sulfate, palladium on barium carbonate, etc.], nickel catalyst [e.g. reduced nickel, nickel oxide, Raney nickel, etc.], cobalt catalyst [e.g. reduced cobalt, Raney cobalt, etc.], iron catalyst [e.g. reduced iron, Raney iron, etc.], copper catalyst [e.g. reduced copper, Raney copper, Ullman copper, etc.] or the like.

The reaction of this process is usually carried out in a solvent such as water, alcohol [e.g. methanol, ethanol, propanol, etc.], acetic acid, diethyl ether, dioxane, tetrahydrofuran, etc. or a mixture thereof.

The reaction is carried out under cooling to heating.

Process D

Step 1

The compound [IX] or its salt can be prepared by hydrogenating a compound [VIc] or its salt.

As suitable examples of the salts of the compounds [VIc] and [IX], there may be mentioned the acid addition salt as given for the compound [I].

This reaction can be carried out in substantially the same manner as that of Process C, and therefore the reaction mode and reaction conditions of this reaction can be referred to those as explained in

Process C.

Step 2

The compound [X] or its salt can be prepared by subjecting a compound [IX] or its salt to introduction reaction of the amino protective group.

As suitable examples of the salt of the compound [X], there may be mentioned the acid addition salt as given for the compound [I].

This reaction can be carried out by a conventional manner, and the reaction mode and reaction conditions such as reagent [e.g. acylating agent, alkylating agent, base, etc.], solvent or reaction temperature, can be referred to those of the conventional introduction reaction of the amino protective group.

Step 3

The compound [XI] or its salt can be prepared by nitrating a compound [X] or its salt.

As suitable examples of the salt of the compound [XI], there may be mentioned the acid addition salt as given for the compound [I].

Suitable nitrating agents to be used in this reaction may be a combination of nitric or nitrate compound [e.g. nitric acid, conc. nitric acid, fuming nitric acid, nitric anhydride, sodium nitrate, potassium nitrate, etc.] and an acid [e.g. sulfuric acid, acetic acid, propionic acid, etc.], nitryl compound [e.g. nitryl pyrosulfate, nitryl tetrafluoroborate, etc.] or the like.

This reaction may be carried out with or without solvent such as tetramethylsulfone, tetrachloromethane, methylene chloride, acetic acid, propionic acid or any other organic solvent which does not adversely influence the reaction. In case that the above-mentioned nitrating agent is liquid, it may be used as a solvent.

The reaction temperature is not critical, and the reaction can be carried out under cooling to heating.

In the course of this reaction, the amino protective group may be also eliminated, and such reaction is included within the scope of this reaction.

Step 4

The compound [VId] or its salt can be prepared by oxidizing a compound [XI] or its salt.

As suitable examples of the salt of the compound [VId], there may be mentioned the acid addition salt as given for the compound [I].

The oxidation reaction can be carried out by a conventional method which is applied for the transformation of an indoline ring to an indole ring, for example, by using an oxidizing agent such as manganese dioxide, nickel peroxide, sulfur powder, 2,3-dichloro-5,6-dicyano-1,4-benzoquinone, potassium permanganate, palladium on carbon or the like.

The present reaction is usually carried out in a solvent such as chloroform, pyridine, ethyl acetate, acetone, benzene, toluene, nitrobenzene or any other solvent which does not adversely affect the reaction.

The reaction temperature is not critical and the reaction is preferably carried out at ambient temperature or under warming or heating.

Process E

The compound [IVa] or its salt can be prepared by subjecting a compound [VIe] or its salt to elimination reaction of the amino protective group.

As suitable examples of the salts of the compounds [IVa] and [VIe], there may be mentioned the same kinds of salt as given for the compound [I].

This elimination reaction can be carried out by a conventional manner, and the reaction mode [e.g. hydrolysis, reduction, etc.] and the reaction conditions e.g. acid, base, catalyst, solvent, reaction temperature, etc.] of this reaction can be referred to those of the conventional elimination reaction of the amino protective group.

The starting compound [V], wherein A is trimethylene, can also be prepared by processes as illustrated in the following reaction schemes.

Process F

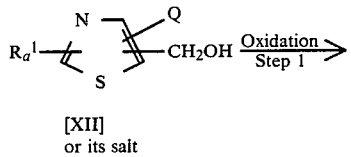

[XII]
or its salt

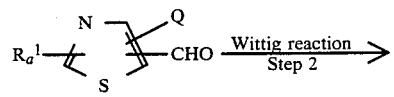

[XIII]
or its salt

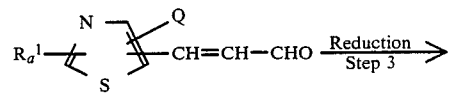

[XIV]
or its salt

-continued
Process F

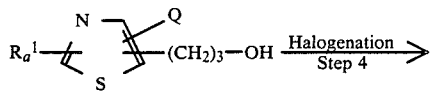

[XV]
or its salt

Halogenation
Step 4

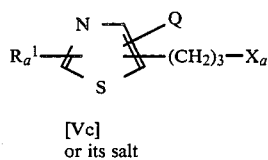

[Vc]
or its salt wherein $X_a$ is halogen, and
$R_a^1$ and Q are each as defined above.

Step 1

The compound [XIII] or its salt can be prepared by oxidizing a compound [XII] or its salt.

The present reaction can be conducted according to a conventional method oxidizing a hydroxymethyl group to give a formyl group, e.g., the oxidation using an oxidizing agent such as sodium metaperiodate, manganese dioxide, lead tetraacetate, potassium permanganate, chromium trioxide and the like. The reaction is usually conducted in a solvent such as water, methanol, ethanol, tetrahydrofuran, ethyl acetate, chloroform or any other solvent which does not adversely affect the reaction, or mixture thereof.

The reaction temperature is not critical and the reaction is preferably carried out under cooling, at room temperature or under heating.

Step 2

The compound [XIV] or its salt can be prepared by subjecting a compound [XIII] or its salt to Wittig reaction.

The reagent used in this Wittig reaction is for example, formylmethylidenetriphenylphosphorane.

This reaction can be carried out by a conventional manner, and the reaction mode and reaction conditions can be referred to those of the conventional Wittig reaction.

Step 3

The compound [XV] or its salt can be prepared by reducing a compound [XIV] or its salt.

This reaction can be carried out in substantially the same manner as that of Process C, and therefore the reaction mode and reaction conditions of this reaction [e.g. reducing agent, solvent, reaction temperature, etc.] can be referred to those as explained in Process C.

In certain reaction conditions, the following compounds may be obtained as intermediates.

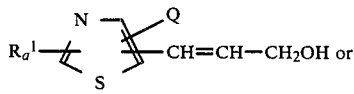

or

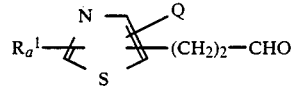

wherein $R_a^1$ and Q are each as defined above.

In such cases, the compound [XV] can be prepared by further reducing said intermediates in the same or different reaction conditions, which is also included within the scope of the present reaction.

Step 4

The compound [Vc] or its salt can be prepared by reacting a compound [XV] or its salt with a halogenating agent.

Suitable examples of the halogenating agent to be used in this process may include a conventional ones such as phosphorus oxyhalide [e.g. phosphorus oxybromide, phosphorus oxychloride, etc.], phosphorus pentahalide [e.g. phosphorus pentabromide, phosphorus pentachloride, phosphorus pentafluoride, etc.], phosphorus trihalide [e.g. phosphorus tribromide, phosphorus trichloride, phosphorus trifluoride, etc.], thionyl halide [e.g. thionyl chloride, thionyl bromide, etc.], triphenylphosphine dihalide [e.g. triphenylphosphine dichloride, triphenylphosphine dibromide, etc.], or the like.

This reaction is usually carried out in a conventional solvent such as methylene chloride, chloroform, carbon tetrachloride, benzene, tetrahydrofuran, dimethylformamide, dimethyl sulfoxide or any other organic solvent which does not adversely influence the reaction. In case that the halogenating agent is liquid, it can be used as a solvent.

The reaction temperature is not critical, and the reaction can be carried out under cooling to heating.

In this process, as suitable examples of the salts of the compounds [XII] to [XV] and [Vc], there may be mentioned the same kinds of salt as given for the compound [I].

The compounds obtained by the above Processes 1 to 8 and A to F can be isolated and purified by a conventional method such as pulverization, recrystallization, column chromatography, reprecipitation or the like.

It is to be noted that each of the object compound [I] and the starting compounds may include one or more stereoisomer due to asymmetric carbon atom(s) and all such isomers and mixture thereof are included within the scope of this invention.

The new thiazole compound [I] and pharmaceutically acceptable salts thereof possess antiallergic activity and are useful for a therapeutic treatment or prophylaxis of allergic disease such as allergic asthma, allergic rhinitis, allergic conjunctivitis or chronic urticaria.

The compound [I] and a pharmaceutically acceptable salt thereof of this invention can be used in the form of conventional solid, semisolid or liquid pharmaceutical preparations in admixture with conventional organic or inorganic carriers or excipients suitable for oral, parenteral or external application. The active ingredients may be admixed with conventional, nontoxic, pharmaceutically acceptable carriers having the form of, for example, tablets, pellets, capsules, patches, suppositories, solutions, emulsions or suspensions or any other form suitable for use. Usable carriers are not limited to any particular species. Thus, conventional carriers such as water, glucose, lactose, gum arabic, gelatin, mannitol, starch paste, magnesium trisilicate, talc, corn starch, keratin, colloidal silica, potato starch and urea and other carriers suitable for the manufacture of solid, semisolid or liquid preparations can be used. Furthermore, auxiliaries, stabilizers, thickening agents and colorants as well as aromas may be added.

The dose or therapeutically effective amount of the object compounds [I] of this invention may vary depending on the age and symptoms of each individual patient to be treated. Generally, the active ingredients are administered for disease treatment in a daily dose of about 0.1–100 mg/kg, preferably 0.1–10 mg/kg.

In order to illustrate the usefulness of the object compound [I], the pharmacological test data of some representative compounds of the compound [I] are shown in the following.

Test Compounds

Compound A: 2-Acetylamino-4-[4-(3-indolyl)-piperidinomethyl]thiazole
Compound B: 4-[4-(3-Indolyl)piperidinomethyl]-2-mesylaminothiazole
Compound C: 4-[2-[4-(3-Indolyl)piperidino]ethyl]2-mesylaminothiazole
Compound D: 4-[4-(3-Indolyl)piperidinomethyl]-2-propionylaminothiazole
Compound E: 4-[4-(3-Indolyl)piperidinomethyl]-2-isobutyrylaminothiazole
Compound F: 4-[3-[4-(3-Indolyl)piperidino]propyl]-2-aminothiazole
Compound G: 4-[3-[4-(3-Indolyl)piperidino]propyl]-2-mesylaminothiazole
Compound H: 4-[4-(3-Indolyl)piperidinomethyl]-2-butyrylaminothiazole
Compound I: 4-[4-(3-Indolyl)piperidinomethyl]-2-cyclopropylcarbonylaminothiazole
Compound J: 4-[4-(3-Indolyl)piperidinomethyl]-2-ethoxycarbonylaminothiazole
Compound K: 4-[4-(5-Nitro-3-indolyl)piperidinomethyl]-2-propionylaminothiazole Test 1

Antagonistic action on anaphylactic asthma in guinea pigs

Male Hartley-strain guinea pigs weighing 305–400 g were used. These animals were sensitized by intravenous injection of 0.5 ml/animal of rabbit antiserum to egg-white albumin (PCA antibody titer 4,000). After 24 hours, the animals were housed individually in 5.3-liter plastic chambers. Using a commercial sprayer, a 5% egg-white albumin solution was sprayed in the form of an aerosol into each chamber at a rate of 0.16 ml/min for 2 minutes. Thirty minutes prior to the spraying of the egg-white albumin solution, the test compound was administered orally in varied concentrations. Each dosed group consisted of 5 animals. The prophylactic effect to anaphylaxis was expressed in terms of the $ED_{50}$ value determined on the basis of the number of guinea pigs which had survived for not less than 2 hours after antigen spraying for each administration concentration of the test compound. The values thus obtained are given in the following table.

| Test Compound | Test Results Prophylactic Effect $ED_{50}$ (mg/kg) |
| --- | --- |
| A | 0.95 |
| B | 0.086 |
| C | 0.02 |
| D | 0.92 |
| F | 0.3 |
| G | 0.03 |

Test 2

Anti-SRS-A actityty

Peritoneal exudate cells were collected from glycogen-injected SD rats and adjusted to $1 \times 10^7$ cells/ml with Tyrode's solution. One milliliter of the cell suspension was incubated with indomethacin (10 μg/ml and each varied concentration of the test compound for 10 minutes and, then, further incubated with $Ca^{++}$-ionophore (A23187, 1 μg/ml) for 10 minutes. The supernatant was collected by centrifugation and the SRS-A (slow-reacting substance of anaphylaxis) activity was determined in terms of contractility of the isolated guinea pig ileum in the presence of mepyramine, atropine and methysergide.

The results were expressed in terms of the 50% inhibitory concentration to SRS-A synthesis or release from peritoneal exudate cells.

| Test Compound | Test results Inhibitory Concentration $IC_{50}$ (μg/ml) |
| --- | --- |
| D | 0.89 |
| E | 0.75 |
| H | 0.18 |
| I | 0.077 |
| J | 0.36 |
| K | 0.22 |

The following Preparations and Examples are given for the purpose of illustrating the present invention in more detail.

Preparation 1

A mixture of 2-amino-4-chloromethylthiazole hydrochloride (1 g) and pivalic anhydride (5 ml) was stirred at 115° C. for 2 hours. The reaction mixture was cooled and filtered and the insoluble material was washed with diethyl ether. The filtrate and washings were combined and concentrated under reduced pressure. The residue was washed with diethyl ether and dried to give 2-pivaloylamino-4-chloromethylthiazole (0.47 g).

IR (Nujol): 3270, 1658, 1535, 1152, 990, 932, 720 cm$^{-1}$.

NMR (CDCl$_3$, δ): 1.33 (9H, s), 4.57 (2H, s), 6.90 (1H, s), 9.00 (1H, br s).

Preparation 2

A mixture of 2-amino-4-chloromethylthiazole hydrochloride (2 g) and benzoic anhydride (10 g) was stirred at 116° C. for 3 hours and 40 minutes. The reaction mixture was diluted with n-hexane (200 ml) and refluxed for 30 minutes, followed by cooling. The resulting precipitate was collected by filtration and washed with n-hexane to give a crude product. This crude product was subjected to column chromatography on silica gel and elution was carried out with chloroform to give 2-benzoylamino-4-chloromethylthiazole as a pure product (1.28 g).
mp: 129–131° C.
IR (Nujol): 3370, 1673, 1293, 710 cm$^{-1}$.
NMR (CDCl$_3$, δ): 4.45 (2H, s), 6.95 (1H, s), 7.3–8.3 (6H, m).

Preparation 3

To a mixture of 2-amino-4-chloromethylthiazole hydrochloride (2 g), anhydrous pyridine (3.2 g) and anhydrous N,N-dimethylformamide (10 ml) was slowly added acetic formic anhydride (1.7 g) with stirring at 0° to 5° C. After one hour of stirring, the reaction mixture was poured into cold water and extracted with ethyl acetate. The extract was washed with 1N hydrochloric acid and aqueous sodium chloride solution successively and dried over magnesium sulfate. The solvent was then distilled off and the residue was collected and dried to give 2-formylamino-4-chloromethylthiazole (0.94 g).
mp: 173–174° C. (dec.).
IR (Nujol): 3165, 3120, 1690, 1565, 1288, 850, 720 cm$^{-1}$.
NMR (DMSO-d$_6$, δ): 4.74 (2H, s), 7.30 (1H, s), 8.48 (1H, s), 12.30 (1H, br s).

Preparation 4

To a mixture of 2-amino-4-chloromethylthiazole hydrochloride (5 g), anhydrous pyridine (5 ml) and anhydrous N,N-dimethylformamide (25 ml) was slowly added 3,3-dimethylbutyryl chloride (4.4 g) with stirring at 0° to 3° C. After an hour of stirring, the reaction mixture was poured into ice water. The resulting precipitate was collected, washed with water and dried to give 2-(3,3-dimethylbutyrylamino)-4-chloromethylthiazole (6.62 g).
mp: 165°–168° C.
IR (Nujol): 3170, 1650, 1275, 1130, 960, 740 cm$^{-1}$.
NMR (DMSO-d$_6$, δ): 1.02 (9H, s), 2.32 (2H, s), 4.71 (2H, s), 7.20 (1H, s), 12.12 (1H, s).

Preparation 5

To a mixture of 2-amino-4-chloromethylthiazole hydrochloride (50 g), anhydrous N,N-dimethylformamide (250 ml) and anhydrous pyridine (50 ml) was added dropwise propionyl chloride (30 g) keeping the temperature below 3° C. with stirring and the mixture was stirred for 20 minutes at the same temperature. The reaction mixture was poured into ice water (1500 ml) and stirred. The crystal was collected by filtration and washed with water to give 2-propionylamino-4-chloromethylthiazole (28.15 g).
IR (Nujol): 3300, 1698, 1553, 1270, 710 cm$^{-1}$.
NMR (DMSO-d$_6$, δ): 1.23 (3H, t, J=7.2 Hz), 2.53 (2H, q, J=7.2 Hz), 4.55 (2H, s), 6.94 (1H, s), 10.19 (1H, br s).

The following compounds (Preparations 6 to 16) were obtained according to similar manners to those of Preparations 4 and 5.

Preparation 6

2-Valerylamino-4-chloromethylthiazole
mp: 111°–116° C.
IR (Nujol): 3260, 1694, 1550, 1165, 710, 663 cm$^{-1}$.
NMR (DMSO-d$_6$, δ): 0.8–2.7 (9H, m), 4.70 (2H, s), 7.16 (1H, s), 12.23 (1H, s).

Preparation 7

2-Phenylacetylamino-4-chloromethylthiazole
mp: 100°–103° C.
IR (Nujol): 3180, 3060, 1655, 1335, 1310, 1140, 785, 730, 690 cm$^{-1}$.
NMR (DMSO-d$_6$, δ): 3.79 (2H, s), 4.73 (2H, s), 7.26 (1H, s), 7.36 (5H, s), 12.50 (1H, s).
Mass (m/e): 266 (M$^{30}$), 268 (M$^+$+2).

Preparation 8

2-Butyrylamino-4-chloromethylthiazole
mp: 115°–117° C.
IR (Nujol): 3260, 1690, 1550, 1265, 710, 660 cm$^{-1}$.
NMR (DMSO-d$_6$, δ): 0.90 (3H, t, J=7 Hz), 1.63 (2H, sextet, J=7 Hz), 2.40 (2H, t, J=7 Hz), 4.68 (2H, s), 7.16 (1H, s), 12.20 (1H, s).
Mass (m/e): 218 (M$^+$), 220 (M$^{30}$+2).

Preparation 9

2-Cyclopropylcarbonylamino-4-chloromethylthiazole
mp: 177°–178° C.
IR (Nujol): 3190, 3090, 1657, 1553, 1197, 710 cm$^{-1}$.
NMR (CDCl$_3$, δ): 0.8–1.8 (5H, m), 4.57 (2H, s), 6.90 (1H, s), 9.80 (1H, br s).

Preparation 10

2-Ethoxycarbonylamino-4-chloromethylthiazole
IR (Nujol): 3175, 1716, 1573, 1290, 1245, 706 cm$^{-1}$.
NMR (DMSO-d$_6$, δ): 1.27 (3H, t, J=6.6 Hz), 4.23 (2H, q, J=6.6 Hz), 4.69 (2H, s), 7.23 (1H, s).
Mass (m/e): 220 (M$^+$).

Preparation 11

2-[(2R)-2-Acetoxypropionylamino]-4-chloromethylthiazole
IR (Nujol): 1744, 1705, 1547, 1230 cm$^{-1}$.
NMR (CDCl$_3$, δ): 1.55 (3H, d, J=7.2 Hz), 2.16 (3H, s), 4.54 (2H, s), 5.38 (1H, q, J=7.2 Hz), 6.90 (1H, s), 9.5 (1H, br s).
$[\alpha]_D^{24.5}$=36° (c=0.1, DMF).

Preparation 12

2-(2S)-2-Acetoxypropionylamino]-4-chloro-methylthiazole
IR (Nujol): 1744, 1705, 1547, 1230 cm$^{-1}$

Preparation 13

2-(3-Methoxypropionylamino)-4-chloromethylthiazole
mp: 110°–113° C. (recrystallized from ethyl acetate),
IR (Nujol): 3190, 3075, 1658, 1565, 1113, 774 cm$^{-1}$.
NMR (DMSO-d$_6$, δ): 2.76 (2H, t, J=6.3 Hz), 3.46 (3H, s), 3.76 (2H, t, J=6.3 Hz), 4.60 (2H, s), 6.95 (1H, s), 9.87 (1H, br s).
Mass (m/e): 234 (M$^+$).

Preparation 14

2-(3-Acetoxypropionylamino)-4-chloromethylthiazole
mp: 118°–119° C. (recrystallized from chloroform-tetrachloromethane).
IR (Nujol): 3200, 3090, 1740, 1660, 1565 cm$^{-1}$. NMR (DMSO-d$_6$, δ): 1.98 (3H, s), 2.77 (2H, t, J=6.0 Hz), 4.28 (2H, t, J=6.0 Hz), 4.70 (2H, s), 7.23 (1H, s), 9.27 (1H, br s).
Mass (m/e): 262 (M$^+$).

Preparation 15

2-(3-Methoxycarbonylpropionylamino)-4-chloromethylthiazole
mp: 135°–138° C. (dec.).
IR (Nujol): 3275, 3225, 1735, 1695, 1560 cm$^{-1}$.

NMR (DMSO-d6, δ): 2.69 (4H, s), 3.62 (3H, s), 4.72 (2H, s), 7.22 (1H, s), 12.25 (1H, br).
Mass (m/e): 262 (M+).

Preparation 16

2-(N-Methyl-N-propionylamino)-4-chloromethylthiazole

IR (Nujol): 3100, 1672, 1123, 790, 713 cm$^{-1}$.
NMR (CDCl3, δ): 1.27 (3H, t, J=8.0 Hz), 2.68 (2H, q, J=8.0 Hz), 3.72 (3H, s), 4.62 (2H, s), 6.97 (1H, s).

Preparation 17

To a solution of 2-amino-4-chloromethylthiazole hydrochloride (0.5 g) in N,N-dimethylformamide (5 ml) was added methyl isocyanate (0.17 g) in the presence of pyridine (0.24 ml). After 4 hours, methyl isocyanate (0.1 g) was further added. After 1 hour, methyl isocyanate (0.1 g) was added again and the reaction mixture was heated at 50° C. for 3.5 hours. The reaction mixture was then poured into water (20 ml) and extracted with ethyl acetate (30 ml×2). The organic layer was washed with a saturated aqueous solution of sodium chloride and dried over magnesium sulfate. The solvent was distilled off and the residue was crystallized from a mixture of ethanol and n-hexane to give 2-(3-methylureido)-4-chloromethylthiazole (230 mg).

IR (Nujol): 3400, 3250, 3100, 1705, 1650 cm$^{-1}$.
NMR (DMSO-d6, δ): 2.67 (3H, d, J=5.0 Hz), 4.63 (2H, s), 6.4 (1H, br s), 7.03 (1H, s), 10.58 (1H, br s).
Mass (m/e): 205 (M+).

Preparation 18

A mixture of 3-(1-acetyl-4-piperidyl)indole (10.0 g), bromobenzene (6.48 g), potassium carbonate (5.70 g) and copper(II) oxide (0.26 g) in anhydrous N,N-dimethylformamide (10 ml) was refluxed for 30 minutes. The reaction mixture was cooled and diluted with chloroform, and the insoluble material was filtered off. The filtrate was concentrated under reduced pressure and the residue was subjected to column chromatography on alumina (400 g) followed by elution with a mixture of toluene and ethyl acetate (20:1 V/V). The fractions containing the desired compound were combined and concentrated under reduced pressure to give 3-(1-acetyl-4-piperidyl)-1-phenylindole (10.19 g).

IR (film): 1640, 1600, 1500, 1220, 745, 700 cm$^{-1}$.
NMR (CDCl3, δ): 1.4–3.5 (7H, m), 2.11 (3H, s), 3.93 (1H, br d, J=13.5 Hz), 4.77 (1H, br d, J=13.5 Hz), 7.08 (1H, s), 7.45 (5H, s), 7.0–7.8 (4H, m).
Mass (m/e) : 318 (M+).

Preparation 19

A mixture of 3-(1-acetyl-4-piperidyl)-1-phenylindole (5.0 g) and 2N aqueous sodium hydroxide solution (30 ml) in ethanol (30 ml) was refluxed for 7.5 hours. Then, 2N aqueous sodium hydroxide (30 ml) was further added and the mixture was refluxed for another 5 hours. Ethanol was then distilled off and the oily residue was extracted with a mixture of chloroform and methanol (30:1 V/V). The extract was washed with water, dried over magnesium sulfate and concentrated under reduced pressure. The residue was subjected to column chromatography on alumina (500 g) and elution was carried out with a mixture of chloroform and methanol (100:1 to 5:1 V/V). The fractions containing the desired compound were combined and the solvent was distilled off under reduced pressure to give 1-phenyl-3-(4-piperidyl)indole (3.0 g). The following physical data are those of the hydrochloride.

mp: 279°–282° C.
IR (Nujol): 2800–2300, 1595, 1500, 1230, 780, 750, 700 cm$^{-1}$.
NMR (CF3COOD, δ): 1.8–4.0 (9H, m), 7.0–8.0 (5H, m), 7.45 (5H, s).
Mass (m/e): 276 (M+$^{-HCl}$).

Preparation 20

3-(1-Acetyl-1,4-dihydro-4-pyridyl)-5-methoxyindole (3.0 g) was dissolved in hot ethanol (150 ml) and hydrogenation was carried out with Adams catalyst (0.25 g). The mixture was filtered and the filtrate was concentrated under reduced pressure to give a residue containing 3-(1-acetyl-4-piperidyl)-5-methoxyindole. This residue was diluted with 2N aqueous sodium hydroxide solution (22 ml) and ethanol (30 ml) and refluxed for 18 hours. Ethanol was then distilled off and the residue was cooled. The precipitate was collected by filtration and recrystallized from a mixture of ethanol and water to give 5-methoxy-3-(4piperidyl)indole (1.92 g).

mp: 173–175° C.,
IR (Nujol): 3310, 1215, 1030, 795 cm$^{-1}$.
NMR (DMSO-d6, δ): 1.3–2.1 (4H, m), 2.27 (1H, s), 2.4–3.3 (5H, m), 3.72 (3H, s), 6.64 (1H, dd, J=3 Hz and 9 Hz), 6.95 (2H, d, J=1.5 Hz), 7.16 (1H, d, J=9 Hz), 10.48 (1H, s).
Mass (m/e): 230 (M+).

Preparation 21

To a solution of 3-(1-acetyl-4-piperidyl)indole (48.2 g) in acetic acid (1 l) was added sodium cyanoborohydride (95 g) at 15° to 20° C. slowly over a period of 1.5 hours with stirring. The mixture was further stirred at ambient temperature for 3 hours, after which a further amount (10 g) of sodium cyanoborohydride was added. The mixture was stirred for 1 hour and the reaction mixture was diluted with water (500 ml), concentrated under reduced pressure, and allowed to stand overnight. To this reaction mixture was added 2N aqueous sodium hydroxide solution (1.5 l), and the mixture was extracted with ethyl acetate (1 l) 3 times. The extract was washed with a saturated aqueous solution of sodium chloride and dried over magnesium sulfate. The solvent was distilled off and the residue was dissolved in a mixture of tetrahydrofuran (200 ml) and 2N aqueous sodium hydroxide solution (300 ml). The solution was stirred at ambient temperature for 2 hours, after which it was concentrated under reduced pressure. The residue was extracted with ethyl acetate (600 ml) and the extract was washed with a saturated aqueous solution of sodium chloride and dried over magnesium sulfate. The solvent was distilled off and the residue was subjected to column chromatography on silica gel, elution being carried out with a mixture of chloroform and methanol (50:1 V/V) to give 3-(1-acetyl-4-piperidyl)indoline (41.1 g).

IR (film): 3340, 3000, 1640–1605 (broad ) cm$^-$.
NMR (CDCl13, δ): 2.04 (3H, s), 1.0–4.8 (13H, m), 6.4–7.2 (4H, m).

Preparation 22

A mixture of 3-(1-acetyl-4-piperidyl)indoline (41.1 g) and acetic anhydride (300 ml) was refluxed for 3 hours. The excess acetic anhydride was distilled off under reduced pressure and the residue was dissolved in ethyl acetate (500 ml). The solution was washed with a saturated aqueous solution of sodium hydrogen carbonate (100 ml), water (100 ml) and a saturated aqueous solution of sodium chloride successively and dried over magnesium sulfate. The solvent was distilled off and the residue was subjected to column chromatography on silica gel, elution being carried out with a mixture of chloroform and methanol (40:1 V/V) to give 3-(1-acetyl-4-piperidyl)-1-acetylindoline (32 g).

mp: 123°-124° c (recrystallized from ethanol-diisopropylether).

IR (Nujol): 1655, 1640, 1485, 1410, 760 cm$^{-1}$.

NMR (DMSO-$d_6$, δ): 1.93 (3H, s), 2.15 (3H, s), 0.9-4.6 (12H, m), 6.8-7.3 (3H, m), 7.94 (1H, d, J=7.4 Hz).

Mass (m/e): 286 (M+).

Preparation 23

To a solution of 3-(1-acetyl-4-piperidyl)-1acetylindoline (0.3 g) in conc. sulfuric acid (5 ml) was added potassium nitrate (0.12 g) in small portions at a temperature not exceeding 10° C. with stirring. The mixture was stirred at the same temperature for 1 hour and at ambient temperature for 7 hours. The reaction mixture was poured into ice and allowed to stand at ambient temperature for 3 days. The aqueous solution was neutralized with 2N aqueous sodium hydroxide solution and extracted with ethyl acetate. The extract was washed with a saturated aqueous solution of sodium chloride and dried over magnesium sulfate. The solvent was distilled off and the residue was subjected to column chromatography on silica gel, followed by elution with a mixture of chloroform and methanol to give 3-(1-acetyl-4-piperidyl)-5-nitroindoline (0.12 g).

mp: 174-177° C. (recrystallized from ethanol-water).

IR (Nujol): 3240, 1620, 1610, 1310, 1280, 1260 cm$^{-1}$.

NMR (DMSO-$d_6$, δ): 1.95 (3H, s), 0.9-4.7 (12H, m), 6.37 (1H, d, J=9.0 Hz), 7.16 (1H, s), 7.73 (1H, d, J=2.0 Hz), 7.86 (1H, dd, J=9.0 Hz and 2.0 Hz)

Mass (m/e): 289 (M+).

Preparation 24

A mixture of 3-(1-acetyl-4-piperidyl)-5-nitroindoline (10.0 g), manganese dioxide (17 g) and nitrobenzene (100 ml) was heated at 150° C. for 1 hour, with nitrogen gas being bubbled into the reaction mixture. The reaction mixture was cooled and the insoluble material was filtered off. The residue was washed with a mixture of chloroform and methanol (10:1 V/V) and the washings and the filtrate were combined and concentrated. The residue was dissolved in a mixture of chloroform and methanol (400 ml, 1:1 V/V) and the insoluble material was filtered off. The filtrate was concentrated to give 3-(1-acetyl-4-piperidyl)-5-nitroindole (4.67 g).

mp: 238-241° C. (recrystallized from methanol).

IR (Nujol): 3250, 1625, 1615, 1515, 1330, 1110, 1000, 740 cm$^{31}$ $^1$.

NMR (DMSO-$d_6$, δ): 2.02 (3H, s), 1.2-4.7 (9H, m), 7.3-8.5 (4H, m), 11.49 (1H, br s).

Mass (m/e): 287 (M+).

Preparation 25

A mixture of 3-(1-acetyl-4-piperidyl)-5-nitroindole (4 g), 2N aqueous sodium hydroxide solution (100 ml) and ethanol (100 ml) was refluxed for 7 hours. The reaction mixture was cooled and the resulting precipitate was collected by filtration. This solid was recrystallized from ethanol-water to give 3-(4-piperidyl)-5-nitroindole (2.64 g).

mp: 233-239° C. (dec.).

IR (Nujol): 3350, 3140, 1520, 1340, 1330, 1315, 1260, 1100 cm$^{-1}$,

NMR (DMSO-$d_6$, δ): 1.3-3.6 (10H, m), 7.28 (1H, s), 7.42 (1H, d, J=9.0 Hz), 7.89 (1H, dd, J=2.0 Hz and 9.0 Hz), 8.44 (1H, d, J=2.0 Hz). Mass (m/e) : 245 (M+).

Preparation 26

(1) A mixture of 2-amino-4-chloromethylthiazol hydrochloride (69 g) and water (500 ml) was refluxed for 1 hour and the reaction mixture was concentrated. The residue was adjusted to pH 7.5 with a solution of potassium hydroxide (37 g) in methanol (300 ml) under ice-cooling with stirring. The insoluble material was filtered off and the filtrate was concentrated to give a residue including 2-amino-4-hydroxymethylthiazole. To the residue was added pyridine (20 ml), the mixture was cooled and acetic anhydride (81 ml) was added dropwise thereto over a period of 40 minutes at 7° to 8° C. After allowed to stand overnight, the reaction mixture was concentrated and the residue was dissolved in chloroform (400 ml). The organic solution was washed with 1N hydrochloric acid (150 ml), water (150 ml) and brine successively, and dried over magnesium sulfate. The solvent was evaporated to give 2-acetylamino-4-acetcxymethylthiazole (72.04 g).

IR (Nujol): 3190, 3075, 1741, 1722, 1650, 1580, 1260, 736 cm$^{-1}$.

NMR (CDCl$_3$, δ): 2.08 (3H, s), 2.24 (3H, s), 5.08 (2H, s), 6.90 (1H, s), 10.30 (1H, br)

Mass (m/e): 214 (M$^{30}$) . (2) A mixture of 2-acetylamino-4-acetoxymethylthiazole (72 g), potassium carbonate (23.2 g), methanol (1.1 l) and water (0.1 l) was stirred for 3 hours and 20 minutes at ambient temperature. An insoluble material was filtered off and the filtrate was neutralized with 2N hydrochloric acid and evaporated. To the residue was added a mixture of chloroform and methanol (100 ml, 1:1 V/V) and the mixture was heated. An insoluble material was filtered off and the filtrate was concentrated. The residue was purified by column chromatography on silica gel eluting with a mixture of chloroform and methanol (10:1 V/V) to give 2-acetylamino-4-hydroxymethylthiazole (41.11 g).

IR (Nujol): 3370, 3180, 1658, 1563, 1290, 730 cm$^{-1}$.

NMR (DMSO-$d_6$, δ): 2.14 (3H, s), 4.48 (2H, s), 5.12 (1H, br s), 6.88 (1H, s), 12.0 (1H, br s).

Mass (m/e): 172 (M+).

(3) To a solution of 2-acetylamino-4-hydroxymethylthiazole (41 g) in a mixture of chloroform (2870 ml) and methanol (164 ml) was added manganese dioxide (410 g) with vigorous stirring for 1 hour and 20 minutes. The reaction mixture was filtered and the residue was added to a mixture of chloroform and ethanol (410 ml, 10:1 V/V). The mixture was heated with stirring and filtered. The residue was washed with a mixture of chloroform and ethanol (160 ml, 10:1 V/V). Every filtrates and washings were combined and evaporated to give 2-acetylamino-4formylthiazole (35.04 g).

IR (Nujol): 3180, 3100, 1690, 1670, 1275, 740 cm$^{-1}$.

NMR (DMSO-$d_6$, δ): 2.15 (3H, s), 8.23 (1H, s), 9.77 (1H, s), 12.37 (1H, br s).

(4) A mixtuxe of 2-acetylamino-4-formylthiazole (6.05 g), formylmethylidenetriphenylphosphorane (10.82 g) and chloroform (360 ml) was refluxed for 4 hours. The precipitates were collected by filtration and washed with chloroform to give 2-acetylamino-4-(2-formylvinyl)thiazole (4.52 g).

The filtrates and the washings were combined, evaporated and allowed to stand to give the same compound (0.57 g).

mp: 262.5°–263° C. (recrystallized from ethanol).

IR (Nujol): 3180, 3080, 1666, 1640, 1623, 1120, 756 cm$^{-1}$.

NMR (DMSO-d$_6$, δ): 2.20 (3H, s), 6.67 (1H, dd, J=15.0 and 8.0 Hz), 7.70 (1H, d, J=15.0 Hz), 7.80 (1H, s), 9.72 (1H, d, J=8.0 Hz), 12.30 (1H, br s).

(5) To a solution of 2-acetylamino-4-(2-formylvinyl)-thiazole (2.24 g) in N,N-dimethylformamide was added 10% palladium on carbon (11.2 g) and hydrogen gas was bubbled thereinto for 4.5 hours. The reaction mixture was filtered and the filtrate was concentrated. The residue was purified by column chromatography on silica gel eluting with a mixture of chloroform and methanol (10:1 V/V) to give 2-acetylamino-4-(2-formylethyl)thiazole (2.06 g).

IR (Nujol): 3170, 3060, 1724, 1644, 1379, 718 cm$^{-1}$.

NMR (CDCl$_3$, δ): 2.23 (3H, s), 2.6–3.3 (4H, m), 6.57 (1H, s), 9.80 (1H, d, J=1.0 Hz)

Mass (m/e): 198 (M+)

(6) To a solution of 2-acetylamino-4-(2-formylethyl)-thiazole (2.49 g) in diisopropyl ether (170 ml) was added sodium borohydride (120 mg) under ice-cooling and stirred for 1 hour at the same temperature. The reaction mixture was concentrated and the residue was purified by column chromatography on silica gel eluting with a mixture of chloroform and methanol (20:1 V/V) to give 2-acetylamino-4-(3-hydroxypropyl)thiazole (1.70 g).

IR (Nujol): 3400, 3200, 3080, 1660, 1560 cm$^{-1}$.

NMR (DMSO-d$_6$, δ): 1.6–2.2 (2H, m), 2.5–3.0 (2H, m), 2.12 (3H, s), 3.31 (1H, s), 3.2–3.7 (2H, m), 6.72 (1H, s), 11.77 (1H, s).

Mass (m/e): 200 (M+).

(7) To a suspension of 2-acetylamino-4-(3-hydroxypropyl)thiazole (1.5 g) in chloroform (2 ml) was added thionyl chloride (1.1 ml) and the mixture was warmed at 60° C. After the reaction was finished, the reaction mixture was poured into ice water and neutralized with an aqueous solution of sodium hydrogen carbonate. The mixture was extracted with chloroform and the extract was dried over magnesium sulfate and concentrated to give 2-acetylamino-4-(3-chloropropyl)thiazole (1.50 g).

mp: 113°–115° C. (recrystallized from toluene-n-hexane).

IR (Nujol): 3200, 3060, 1645, 1550 cm$^{-1}$.

NMR (CDCl$_3$, δ): 2.10 (2H, m), 2.23 (3H, s), 2.83 (2H, t, J=8.0 Hz), 3.54 (2H, t, J=8 Hz), 6.55 (1H, s), 9.7 (1H, br).

Mass (m/e): 218 (M+), 176, 114.

EXAMPLE 1

2-Acetylamino-4-chloromethylthiazole (480 mg), 3-(4-piperidyl)indole (500 mg) and sodium hydrogen carbonate (310 mg) was refluxed in a mixture of N,N-dimethylformamide (5 ml) and tetrahydrofuran (7 ml) for 1 hour and 40 minutes. After the reaction mixture cooled to ambient temperature, it was concentrated under reduced pressure. After addition of water (50 ml), the residue was extracted with ethyl acetate (50 ml) twice. The extract was washed with a saturated aqueous solution of sodium chloride, dried over magnesium sulfate, and concentrated under reduced pressure. The residue was subjected to column chromatography on silica gel and elution was carried out with a mixture of chloroform and methanol (30:1 V/V). The eluate gave 2-acetylamino-4-[4-(3-indolyl)piperidinomethyl]thiazole (270 mg).

mp: 204°–207° C. (recrystallized from ethanol).

IR (Nujol): 3400, 3165, 1686, 1263, 1004, 758, 747 cm$^{-1}$.

NMR (DMSO-d$_6$, δ): 2.32 (3H, s), 1.4–3.2 (9H, m), 3.52 (2H, s), 6.8–7.65 (6H, m), 10.70 (1H, s), 12.08 (1H, s).

Mass: 354 (M+).

Elemental analysis: C$_{19}$H$_{22}$N$_4$OS: Calcd.: C 64.38, H 6.26, N 15.81, Found: C 64.40, H 6.06, N 15.67.

EXAMPLE 2

2-Acetylamino-4-(2-chloroethyl)thiazole (1 g), 3-(4-piperidyl)indole (0.98 g), sodium hydrogen carbonate (620 mg) and potassium iodide (810 mg) were refluxed in a mixture of tetrahydrofuran (14 ml) and N,N-dimethylformamide (10 ml) for 4 hours and 10 minutes. Thereafter, with additions of 2-acetylamino-4-(2-chloroethyl)thiazole (0.5 g) three times, the mixture was further refluxed for 2 hours and 20 minutes. After cooling to ambient temperature, the reaction mixture was concentrated under reduced pressure. The residue was extracted with a mixture of chloroform and methanol (100 ml, 10:1 V/V) and the extract was washed successively with water and a saturated aqueous solution of sodium chloride, dried over magnesium sulfate, and concentrated under reduced pressure. The residue was subjected to column chromatography on silica gel and elution was carried out with a mixture of chloroform and methanol (10:1 V/V). The eluate gave 2-acetylamino-4-[2-[4-(3-indolyl)piperidino]ethyl]thiazole (500 mg).

mp: 203°–204° C. (recrystallized from ethanol).

Mass: 368 (M+).

IR (Nujol): 3275, 1663, 1560, 1305, 1106, 740 cm$^{-1}$.

NMR (DMSO-d$_6$, δ): 2.13 (3H, s), 1.4–3.4 (13H, m), 6.80 (1H, s), 6.8–7.7 (5H, m), 10.79 (1H, s), 12.03 (1H, br s).

Elemental analysis: C$_{20}$H$_{24}$N$_4$OS: Calcd.: C 65.19, H 6.56, N 15.20, Found: C 65.30, H 6.77, N 15.21.

EXAMPLE 3

A mixture of 2-pivaloylamino-4-chloromethylthiazole (0.42 g), 3-(4-piperidyl)indole (0.34 g), sodium hydrogen carbonate (0.23 g), N,N-dimethylformamide (4.2 ml) and a trace amount of sodium iodide was stirred at 50° C. for 2 hours. The insoluble material was filtered off and the filtrate was washed with a mixture of chloroform and methanol (10:1 V/V). The washings and the filtrate were combined and concentrated under reduced pressure. The residue was subjected to column chromatography on silica gel and recrystallized from ethanol to give 4-[4-(3-indolyl)piperidinomethyl]-2-pivaloylaminothiazole (280 mg).

mp: 93°–96° C.

IR (Nujol): 3235, 1684, 1165, 1148, 1045, 750 cm$^{-1}$.

NMR (CDCl$_3$, δ): 1.33 (9H, s), 1.5–3.4 (9H, m), 3.56 (2H, s), 6.73 (1H, s), 6.9–7.8 (5H, m), 8.10 (1H, br s), 9.00 (1H, br s).

Elemental analysis: C$_{22}$H$_{28}$N$_4$OS·C$_2$H$_5$OH: Calcd.: C 65.12, H 7.74, N 12.65, Found: C 65.11, H 7.77, N 12.60.

EXAMPLE 4

A mixture of 2-cyclopropylcarbonylamino-4-chloromethylthiazole (0.8 g), 3-(4-piperidyl)indole (0.74 g), sodium hydrogen carbonate (0.34 g) and N,N-dimethylformamide (3.7 ml) was heated at 100° C. for 45 minutes.

Thereafter, the procedure of Example 3 was followed to give 4-[4-(3-indolyl)piperidinomethyl]-2-cyclopropylcarbonylaminothiazole (0.41 g).

mp: 120°–132° C. (recrystallized from acetonitrile).

IR (Nujol): 3560, 3420, 1673, 1550, 1270, 1190, 1000 cm$^{-1}$.

NMR (DMSO-d$_6$, δ): 0.6–1.3 (4H, m), 1.5–3.7 (10H, m), 3.57 (2H, s), 6.8–7.8 (6H, m), 10.90 (1H, s), 12.27 (1H, s).

Mass (m/e): 380 (M+).

Elemental analysis: $C_{21}H_{24}N_4OS \cdot H_2O$: Calcd.: C 63.29, H 6.58, N 14.06, Found: C 63.44, H 6.86, N 14.00.

EXAMPLE 5

In a stream of nitrogen gas, a mixture of 2-(3-methylureido)-4-chloromethylthiazole (1.0 g), 3-(4-piperidyl)indole (0.98 g), sodium hydrogen carbonate (0.45 g) and N,N-dimethylformamide (5 ml) was heated at 80° to 90° C. The reaction mixture was then concentrated and the residue was subjected to column chromatography on silica gel. Elution was carried out with a mixture of chloroform and methanol (10:1 V/V). The fractions containing the desired compound were collected and concentrated under reduced pressure. The residue was precipitated with n-hexane to give 4-[4-(3-indolyl)piperidinomethyl]-2-(3-methylureido)thiazole (540 mg).

mp: 222°–224° C. (dec.) (recrystallized from water-ethanol).

IR (Nujol): 3350, 1715, 1680, 1550 cm$^{-1}$.

NMR (DMSO-d$_6$, δ): 1.5–3.2 (12H, m), 3.50 (2H, br s), 6.50 (1H, m), 6.8–7.2 (2H, m), 7.05 (1H, d, J=2.0 Hz), 7.08 (1H, s), 7.38 (1H, dd, J=2.0 Hz and 7.0 Hz), 7.55 (1H, dd, J=2.0 Hz and 7.0 Hz), 10.7 (1H, br s).

Mass (m/e): 369 (M+).

Elemental analysis: $C_{19}H_{23}N_5OS$: Calcd.: C 61.76, H 6.27, N 18.95, Found: C 62.14, H 6.16, N 18.61.

EXAMPLE 6

A mixture of 2-propionylamino-4-chloromethylthiazol (5.11 g), 3-(4-piperidyl)indole (5 g), sodium hydrogen carbonate (2.31 g) and N,N-dimethylformamide (25 ml) was heated at 102° to 103° C. with bubbling nitrogen gas and stirring for 6 hours. The reaction mixture was filtered and the filtrate was concentrated. The residue was subjected to column chromatography on silica gel and the column was eluted with a mixture of chloroform and methanol (10:1 V/V). The fractions containing the desired compound were combined and concentrated and ethanol was added thereto. The solution was concentrated again and the residue was triturated with diisopropyl ether to give 4-[4-(3-indolyl)-piperidinomethyl]-2-propionylaminothiazole (6.50 g).

mp: 191.5°–195° C.

IR (Nujol): 3380, 1673, 1540, 1180, 738 cm$^{-1}$.

NMR (DMSO-d$_6$, δ): 1.07 (3H, t, J=7.2 Hz), 1.2–3.8 (13H, m), 6.8–7.7 (6H, m), 10.66 (1H, br s), 12.05 (1H, br s).

The following compounds (Examples 7 to 51) were obtained according to a similar manner to that of Examples 1,2,3,4,5 or 6.

EXAMPLE 7

2-Acetylamino-4-[3-[4-(3-indolyl)piperidino]propyl]thiazole mp: 168.5°–170° C. (recrystallized from ethanol).

IR (Nujol): 3300, 3100, 1670, 1570, 1300, 985, 750 cm$^{-1}$.

NMR (DMSO-d$_6$, δ): 1.4–3.3 (15H, m), 2.12 (3H, s), 6.70 (1H, s), 6.8–7.7 (5H, m), 10.70 (1H, br s), 12.00 (1H, br s).

Elemental analysis: $C_{21}H_{26}N_4OS$: Calcd.: C 65.94, H 6.85, N 14.65, Found: C 65.76, H 6.36, N 14.46.

EXAMPLE 8

2-Acetylamino-4-[4-(3-indolyl)-1,2,5,6-tetrahydropyridin-1-ylmethyl]thiazole mp: 217°–219° C.

IR (Nujol): 3150, 1653, 1310, 1125, 750 cm$^{-1}$.

NMR (DMSO-d$_6$, δ): 2.14 (3H, s), 2.4–3.5 (6H, m), 3.64 (2H, s), 6.10 (1H, br s), 6.97 (1H,s), 6.9–8.1 (5H, m), 11.05 (1H, br s), 12.00 (1H, br s).

Elemental analysis: $C_{19}H_{20}N_4OS \cdot \frac{1}{3}CHCl_3$: Calcd.: C 59.20, H 5.22, N 14.28, Found: C 58.80, H 5.34, N 14.02.

EXAMPLE 9

4-[4-(3-Indolyl)piperidinomethyl]-2-benzoylaminothiazole mp: 104°–106° C. (recrystallized from ethanol).

IR (Nujol): 3150, 1670, 1300, 1097, 995, 745, 705 cm$^{-1}$.

NMR (CDCl$_3$, δ): 1.4–3.3 (9H, m), 3.37 (2H, s), 6.78 (2H, s), 6.9–8.4 (12H, m).

Elemental analysis: $C_{24}H_{24}N_4OS \cdot C_2H_5OH$: Calcd.: C 67.51, H 6.54, N 12.11, Found: C 67.70, H 6.42, N 12.13.

EXAMPLE 10

4-[4-(3-Indolyl)piperidinomethyl]-2-(3,3-dimethylbutyrylamino)thiazole mp: 224.5°–226° C.

IR (Nujol): 3390, 3248, 1650, 1548, 1327, 740 cm$^{-1}$.

NMR (DMSO-d$_6$, δ): 1.03 (9H, s), 2.33 (2H, s), 1.3–3.3 (9H, m), 3.53 (2H, s), 6.95 (1H, s), 7.0–7.8 (5H, m), 10.75 (1H, s), 12.03 (1H, s).

Elemental analysis: $C_{23}H_{30}N_4OS$: Calcd.: C 67.28, H 7.36, N 13.65, Found: C 67.58, H 6.95, N 13.54.

EXAMPLE 11

4-[4-(3-Indolyl)piperidinomethyl]-2-valerylaminothiazole mp: 142°–144° C.

IR (Nujol): 3240, 1693, 1553, 1105, 745 cm$^{-1}$.

NMR (DMSO-d$_6$, δ): 0.8–3.7 (18H, m), 3.55 (2H, s), 6.92 (1H, s), 6.9–7.7 (5H, m), 10.73 (1H, s), 12.05 (1H, br s).

Elemental analysis: $C_{22}H_{28}N_4OS \cdot C_2H_5OH$: Calcd.: C 65.13, H 7.74, N 12.66, Found: C 64.60, H 7.56, N 12.63.

EXAMPLE 12

4-[4-(3-Indolyl)piperidinomethyl]-2-formylaminothiazole mp: 217°–221° C.

IR (Nujol): 3460, 1690, 1562, 1280, 852, 755 cm$^{-1}$.

NMR (DMSO-d$_6$, δ): 1.5–3.8 (9H, m), 3.51 (2H, s), 6.8–7.7 (6H, m), 8.45 (1H, s), 10.70 (1H, br s), 12.13 (1H, br s).

Elemental analysis: $C_{18}H_{20}N_4OS$: Calcd.: C 63.51, H 5.92, N 16.46, Found: C 63.54, H 5.78, N 16.31.

EXAMPLE 13

4-[4-(3-Indolyl)piperidinomethyl]-2-butyryl-aminothiazole mp: 163°–165° C. (recrystallized from ethanol).

IR (Nujol): 3200 (broad), 1690, 1555, 745 cm$^{-1}$.

NMR (DMSO-d$_6$, δ): 0.90 (3H, t, J=7.5 Hz), 1.07 (3H, t, J=7.5 Hz), 3.53 (2H, s), 4.33 (1H, br s), 6.92 (1H, s), 6.9–7.7 (5H, m), 10.71 (1H, s), 12.02 (1H, s).

Mass (m/e): 382 (M$^+$-C$_2$H$_5$OH).

Elemental analysis: C$_{21}$H$_{26}$N$_4$OS.C$_2$H$_5$OH: Calcd.: C 64.45, H 7.52, N 13.07, Found: C 64.19, H 7.54, N 13.07.

EXAMPLE 14

4-[4-(3-Indolyl)piperidinomethyl]-2-phenylacetylaminothiazole mp: 190°–191° C. (recrystallized from ethanol).

IR (Nujol): 3250, 1660, 1555, 1545, 735 cm$^{-1}$.

NMR (DMSO-d$_6$, δ): 3.52 (2H, s), 3.74 (2H, s), 6.92 (1H, s), 7.31 (5H, s), 6.9–7.7 (5H, m), 10.71 (1H, s), 12.33 (1H, s).

Mass (m/e): 430 (M$^+$).

Elemental analysis: C$_{25}$H$_{26}$N$_4$OS: Calcd.: C 69.74; H 6.09, N 13.01, Found: C 69.48, H 5.93, N 13.16.

EXAMPLE 15

4-[4-(5-Methoxy-3-indolyl)piperidinomethyl]-2-acetylaminothiazole mp: 123°–133° C.

IR (Nujol): 3420, 1690, 1570, 1290, 1220, 810 cm$^{-1}$.

NMR (DMSO-d$_6$, δ): 1.3–2.4 (4H, m), 2.11 (3H, s), 2.5–3.2 (5H, m), 3.34 (2H, s), 3.52 (2H, s), 3.74 (3H, s), 6.70 (1H, dd, J=3 Hz and 9 Hz), 6.90 (1H, s), 6.98 (1H, d, J=3 Hz), 7.03 (1H, d, J=3 Hz), 7.23 (1H, d, J=9 Hz), 10.55 (1H, s), 12.05 (1H, s).

Mass (m/e): 384 (M$^+$-H$_2$O).

Elemental analysis: C$_{20}$H$_{24}$N$_4$O$_2$S.H$_2$O: Calcd.: C 59.68, H 6.51, N 13.92, Found: C 59.70, H 6.61, N 13.70.

EXAMPLE 16

4-[4-(1-Phenyl-3-indolyl)piperidinomethyl]-2-acetylaminothiazole mp: 185°–187° C.

IR (Nujol): 3400–3200 (broad), 1690, 1500, 1265, 745 cm$^{-1}$.

NMR (CDCl$_3$, δ): 1.6–3.3 (9H, m), 2.23 (3H, s), 3.59 (2H, s), 6.77 (1H, s), 7.09 (1H, s), 7.45 (5H, s), 7.0–7.8 (4H, m), 10.0 (1H, br s).

Mass (m/e): 430 (M$^+$).

Elemental analysis: C$_{25}$H$_{26}$N$_4$OS: Calcd.: C 69.74, H 6.09, N 13.01, Found: C 69.78, H 5.92, N 12.72.

EXAMPLE 17

4-[4-(3-Indolyl)piperidinomethyl]-2-methylaminothiazole mp: 145°–147° C. (recrystallized from acetonitrile).

IR (Nujol): 3370, 3230, 1580, 990, 732 cm$^{-1}$.

NMR (DMSO-d$_6$, δ): 1.5–3.2 (9H, m), 2.86 (3H, s), 2.78 (1H, s), 3.39 (2H, s), 6.39 (1H, s), 6.7–7.8 (5H, s), 10.76 (1H, s).

Mass (m/e): 326 (M$^+$).

Elemental analysis: C$_{18}$H$_{22}$N$_4$S: Calcd.: C 66.23, H 6.79, N 17.16, Found: C 66.53, H 6.78, N 17.28.

EXAMPLE 18

4-[4-(3-Indolyl)piperidinomethyl]-2-ethylaminothiazole mp: 159°–160° C. (recrystallized from acetonitrile).

IR (Nujol): 3380, 3210, 1548, 1525, 740, 700 cm$^{-1}$.

NMR (DMSO-d$_6$, δ): 1.29 (3H, t, J=7.0 Hz), 1.5–3.5 (12H, m), 3.40 (2H, s), 6.36 (1H, s), 6.8–7.8 (5H, m), 10.77 (1H, s).

Mass (m/e): 340 (M$^+$),

Elemental analysis: C$_{19}$H$_{24}$N$_4$S: Calcd.: C 67.02, H 7.10, N 16.45, Found: C 67.28, H 7.25, N 16.75.

EXAMPLE 19

4-[4-(3-Indolyl)piperidinomethyl]-2-ethoxycarbonylaminothiazole mp: 85° C. (dec.).

IR (Nujol): 3440, 1725, 1563, 1075, 740 cm$^{-1}$.

NMR (DMSO-d$_6$, δ): 1.27 (3H, t, J=6.4 Hz), 1.5–3.5 (9H, m), 3.52 (2H, s), 4.23 (2H, q, J=6.4 Hz), 6.94 (1H, s), 7.0–7.8 (5H, m), 10.75 (1H, s), 11.60 (1H, br s).

Mass (m/e): 384 (M$^+$).

Elemental analysis: C$_{20}$H$_{24}$N$_4$O$_2$S.1/10CHCl$_3$. Calcd.: C 60.60, H 6.13, N 14.13, Found: C 61.02, H 6.10, N 13.75.

EXAMPLE 20

4-[4-(1-Methyl-3-indolyl)piperidinomethyl]-2-acetylaminothiazole mp: 176°–177° C. (recrystallized from ethanol).

IR (Nujol): 3150, 1690, 1550, 1279, 743 cm$^{-1}$.

NMR (DMSO-d$_6$, δ): 1.5–3.7 (9H, m), 2.16 (3H, s), 3.55 (2H, s), 3.74 (3H, s), 6.8–7.8 (6H, m).

Mass (m/e): 368 (M$^+$).

Elemental analysis: C$_{20}$H$_{24}$N$_4$OS: Calcd.: C 65.19, H 6.56, N 15.20, Found: C 65.24, H 6.22, N 15.08.

EXAMPLE 21

4-[4-(5-Nitro-3-indolyl)piperidinomethyl]-2-propionylaminothiazole mp: 222°–224° C.

IR (Nujol): 3290, 1670, 1575, 1520, 1330, 1250, 1100, 735 cm$^{-1}$.

NMR (DMSO-d$_6$, δ): 1.10 (3H, t, J=7.5 Hz), 2.40 (2H, q, J=7.5 Hz), 1.4–3.5 (9H, m), 3.50 (2H, s), 6.85 (1H, s), 7.3–8.5 (4H, m), 11.48 (1H, br s), 11.91 (1H, br s).

Mass (m/e): 413 (M$^+$).

Elemental analysis: C$_{20}$H$_{23}$N$_5$O$_3$S.1/5C$_2$H$_5$OH: Calcd.: C 57.97, H 5.73, N 16.57, Found: C 57.78, H 5.49, N 16.38.

EXAMPLE 22

4-[4-(3-Indolyl)piperidinomethyl]-2-[(2R)-2-acetoxypropionylamino]thiazole

IR (Nujol): 3430, 1744, 1692, 1550, 1463 cm$^{-1}$.

NMR (CDCl$_3$, δ): 1.55 (3H, d, J=6.9 Hz), 1.6–3.3 (9H, m), 2.17 (3H, s), 3.55 (2H, s), 5.38 (1H, q, J=6.9 Hz), 6.8–8.1 (8H, m).

$[\alpha]_D^{24.5}$ =12.0° (C=0.1, DMF).

Mass (m/e): 426 (M$^+$).

EXAMPLE 23

4-[4-(3-Indolyl)piperidinomethyl]-2-[(2S)-2-acetoxypropionylamino]thiazole

IR (Nujol): 3430, 1744, 1692, 1550, 1463 cm$^{-1}$.

EXAMPLE 24

4-[4-(3-Indolyl)piperidinomethyl]-2-(3-methoxypropionylamino)thiazole mp: 157°–158° C. (recrystallized from methanol).

IR (Nujol): 3200, 1696, 1554, 1106, 740 cm$^{-1}$.

NMR (DMSO-d$_6$, δ): 1.5–3.5 (9H, m), 2.65 (2H, t, J=6.0 Hz), 3.23 (3H, s), 3.52 (2H, s), 3.63 (2H, t, J=6.0 Hz), 6.8–7.6 (6H, m), 10.7 (1H, s), 12.06 (1H, s).

Mass (m/e): 398 (M$^+$).

Elemental analysis: C$_{21}$H$_{26}$N$_4$O$_2$S: Calcd.: C 63.29, H 6.58, N 14.06, Found: C 63.78, H 6.64, N 14.17.

EXAMPLE 25

4-[4-(3-Indolyl)piperidinomethyl]-2-(3-acetoxypropionylamino)thiazole
mp: 73°–75° C.
IR (Nujol): 3610, 3430, 1714, 1680, 1565 cm$^{-1}$.
NMR (DMSO-d$_6$, δ): 1.5–2.4 (6H, m), 2.0 (3H, s), 2.76 (2H, t, J=6.0 Hz), 2.6–3.25 (3H, m), 3.54 (2H, s), 4.28 (2H, t, J=6.0 Hz), 6.95 (1H, s), 7.06 (1H, d, J=2.0 Hz), 6.8–7.15 (2H, m), 7.33 (1H, dd, J=2.0 Hz and 7.0 Hz), 7.51 (1H, dd, J=2.0 Hz and 7.0 Hz), 10.71 (1H, br), 12.17 (1H, br).
Elemental analysis: C$_{22}$H$_{26}$N$_4$O$_3$S.2H$_2$O. Calcd.: C 57.12, H 6.54, N 12.11, Found: C 57.38, H 6.57, N 12.07.

EXAMPLE 26

4-[4-(3-Indolyl)piperidinomethyl]-2-(3-methoxycarbonylpropionylamino)thiazole
mp: 101°–107° C. (recrystallized from water-ethanol).
IR (Nujol): 3410, 1735, 1695, 1585 cm$^{-1}$.
NMR (DMSO-d$_6$, δ): 1.4–2.4 (7H, m), 2.8–3.15 (2H, m), 2.69 (4H, s), 3.54 (2H, s), 3.62 (3H, s), 6.93 (1H, s), 6.8–7.2 (2H, m), 7.07 (1H, d, J=2.0 Hz), 7.34 (1H, dd, J=2.0 Hz and 7.0 Hz), 7.53 (1H, dd, J=2.0 Hz and 7.0 Hz), 10.71 (1H, br), 12.1 (1H, br).
Mass (m/e): 426 (M+), 394.
Elemental analysis: C$_{22}$H$_{26}$N$_4$O$_3$S.H$_2$O: Calcd.: C 59.44, H 6.35, N 12.60, Found: C 59.84, H 6.43, N 12.62.

EXAMPLE 27

4-[4-(3-Indolyl)piperidinomethyl]-2-(N-methyl-N-propionylamino)thiazole
mp: 167°–167.5° C.
IR (Nujol): 3150, 1670, 1490, 1123, 735 cm$^{-1}$.
NMR (DMSO-d$_6$, δ): 1.10 (3H, t, J=7.5 Hz), 1.4–3.4 (9H, m), 2.69 (2H, q, J=7.5 Hz), 3.56 (2H, s), 3.63 (3H, s), 6.8–7.7 (6H, m), 10.70 (1H, s).
Mass (m/e): 382 (M+).
Elemental analysis: C$_{21}$H$_{26}$N$_4$OS: Calcd.: C 65.94, H 6.85, N 14.65, Found: C 66.44, H 6.92, N 14.74.

EXAMPLE 28

4-[4-(3-Indolyl)piperidinomethyl]-2-acetylamino-5-chlorothiazole
mp: 145° C. (dec.) (recrystallized from ethanol).
IR (Nujol): 3440, 1685, 1574, 1300, 740 cm$^{-1}$.
NMR (DMSO-d$_6$, δ): 1.3–3.6 (9H, m), 2.13 (3H, s), 3.55 (2H, s), 6.8–7.7 (5H, m), 10.77 (1H, s).
Mass (m/e): 390 (M++2), 388 (M+).
Elemental analysis: C$_{19}$H$_{21}$ClN$_4$OS.H$_2$O.½C$_2$H$_5$OH. Calcd.: C 56.07, H 5.78, N 13.62, Found: C 56.43, H 5.60, N 13.96.

EXAMPLE 29

2-Amino-4-[4-(3-indolyl)piperidinomethyl]thiazole
mp: 195°–198° C.
IR (Nujol): 3300, 1380, 1330, 1092, 980, 735 cm$^{-1}$.
NMR (DMSO-d$_6$, δ): 1.4–3.4 (1H, m), 6.30 (1H, s), 6.77 (2H, s), 6.8–7.7 (5H, m), 10.7 (1H, s).

EXAMPLE 30

2-Amino-4-[2-[4-(3-indolyl)piperidino]ethyl]thiazole
mp: 173.5°–176.0° C.
IR (Nujol): 3425, 3250, 1615, 1505, 1340, 1120, 750 cm$^{-1}$.
NMR (DMSO-d$_6$, δ): 1.3–3.3 (13H, m), 6.15 (1H, s), 6.74 (2H, s), 6.8–7.7 (5H, m), 10.70 (1H, br s).

EXAMPLE 31

4-[3-[4-(3-Indolyl)piperidino]propyl]-2-aminothiazole
mp: 108°–109° C.
IR (Nujol): 3450, 3100, 1635, 1530 cm$^{-1}$.
NMR (DMSO-d$_6$, δ): 1.5–3.0 (15H, m), 6.03 (1H, s), 6.68 (2H, s), 6.9–7.5 (5H, m).

EXAMPLE 32

4-[4-(3-Indolyl)piperidinomethyl]-2-mesylaminothiazole
mp: 215°–217° C.
IR (Nujol): 3310, 1380, 1260, 1116, 967, 743 cm$^{-1}$.
NMR (DMSO-d$_6$, δ): 1.5–3.3 (9H, m), 2.80 (3H, s), 3.50 (2H, s), 6.68 (1H, s), 6.8–7.7 (5H, m), 10.72 (1H, s).

EXAMPLE 33

4-[2-[4-(3-Indolyl)piperidino]ethyl]-2-mesylaminothiazole
mp: 141°–144° C.
IR (Nujol): 1120, 1100, 968, 740 cm$^{-1}$.
NMR (DMSO-d$_6$, δ): 1.5–3.4 (13H, m), 2.80 (3H, s), 6.41 (1H, s), 6.8–7.8 (5H, m), 10.70 (1H, br s).

EXAMPLE 34

4-[4-(3-Indolyl)piperidinomethyl]-2-isobutyrylaminothiazole
mp: 183°–187° C.
IR (Nujol): 3280, 3100, 1533, 1100, 758 cm$^{-1}$.
NMR (DMSO-d$_6$, δ): 1.14 (6H, d), 1.2–3.7 (12H, m), 6.8–7.7 (6H, m), 10.70 (1H, br s), 12.05 (1H, br s).

EXAMPLE 35

4-[4-(3-Indolyl)piperidinomethyl]-2-ethylsulfonylaminothiazole
mp: 181°–186° C. (recrystallized from ethanol).
IR (Nujol): 3270, 1465, 1110, 1017, 738 cm$^{-1}$.
NMR (DMSO-d$_6$, δ): 1.22 (3H, t, J=7.6 Hz), 1.5–3.7 (11H, m), 3.47 (2H, s), 6.57 (1H, s), 6.9–7.8 (5H, m), 9.46 (1H, br s), 10.78 (1H, s).

EXAMPLE 36

4-[4-(3-Indolyl)piperidinomethyl]-2-isopropylsulfonylaminothiazole hydrochloride
mp: 230°–238° C.
IR (Nujol): 3365, 1540, 1460, 1118, 883, 740 cm$^{-1}$.
NMR (DMSO-d$_6$, δ): 1.24 (6H, d, J=4.2 Hz), 1.8–3.7 (12H, m), 4.27 (2H, s), 6.8–7.0 (6H, m).

EXAMPLE 37

4-[2-[4-(3-Indolyl)piperidino]ethyl]-2-ethylsulfonylaminothiazole hydrochloride
mp: 222°–228° C.
IR (Nujol): 3250, 2650, 1544, 1293, 1117, 890, 743 cm$^{-1}$.
NMR (DMSO-d$_6$, δ): 1.22 (3H, t, J=7.8 Hz), 1.8–4.0 (17H, m), 6.40 (1H, s), 6.7–7.8 (5H, m), 10.75 (1H, br s).

EXAMPLE 38

4-[3-[4-(3-Indolyl)piperidino]propyl]-2-mesylaminothiazole
mp: 210°–214° C.
IR (Nujol): 3350, 1535 cm$^{-1}$.
NMR (DMSO-d$_6$, δ): 1.5–3.3 (15H, m), 2.72 (3H, s), 5.80 (1H, br s), 6.25 (1H, s), 6.9–7.5 (5H, m), 10.7 (1H, br s).

EXAMPLE 39

4-[4-(3-Indolyl)piperidinomethyl]-2-(2-acetoxyacetylamino)thiazole mp: 140°–144° C.

IR (Nujol): 3410, 1750, 1705, 1585 cm$^{-1}$.

NMR (DMSO-d$_6$, δ): 1.5–2.4 (5H, m), 2.13 (3H, s), 2.6–3.9 (4H, m), 3.54 (2H, br s), 4.75 (2H, br s), 6.8–7.2 (2H, m), 7.0 (1H, s), 7.08 (1H, d, J=2.0 Hz), 7.35 (1H, dd, J=2.0 and 7.0 Hz), 7.55 (1H, dd, J=2.0 and 7.0 Hz).

EXAMPLE 40

4-[4-(3-Indolyl)piperidinomethyl]-2-(2-methoxyacetylamino)thiazole hydrochloride mp: 190°–205° C.

IR (Nujol): 3400, 2650, 2550, 1695, 1550 cm$^{-1}$.

NMR (DMSO-d$_6$, δ): 2.08 (3H, s), 4.20 (2H, s), 4.33 (2H, br s), 1.9–3.8 (9H, m), 6.8–7.8 (6H, m), 10.88 (1H, br s), 12.15 (1H( br s).

EXAMPLE 41

4-[4-(5-Amino-3-indolyl)piperidinomethyl]-2-propionylaminothiazole mp: 115°–118° C. (dec.).

IR (Nujol): 3400, 3300, 3200, 1685, 1555, 1350, 1330, 1275, 1200 cm$^{-1}$.

NMR (DMSO-d$_6$, δ): 1.05 (3H, t, J=7.0 Hz), 2.41 (2H, q, J=7 Hz), 1.3–3.6 (9H, m), 3.50 (2H, s), 4.30 (2H, br s), 6.3–7.0 (5H, m), 10.10 (1H, br s), 11.88 (1H, br s).

EXAMPLE 42

4-[4-(5-Acetylamino-3-indolyl)piperidinomethyl]-2-propionylaminothiazole mp: 263°–267° C.

IR (Nujol): 3370, 1680, 1650, 1590, 1560 cm$^{-1}$.

NMR (DMSO-d$_6$, δ): 1.08 (3H, d, J=9.0 Hz), 2.0 (3H, s), 2.35 (2H, q, J=9.0 Hz), 1.4–3.2 (9H, m), 3.48 (2H, s), 6.8–9.56 (5H, m), 10.55 (1H, br s), 11.93 (1H, br s).

EXAMPLE 43

4-[4-(3-Indolyl)piperidinomethyl]-2-(D-lactoylamino)thiazole mp: 213°–216.5° C.

IR (Nujol): 3360, 3190, 1663, 1570, 1138 cm$^{-1}$.

NMR (DMSO-d$_6$, δ): 1.27 (3H, d, J=6.6 Hz), 1.4–3.6 (9H, m), 3.52 (2H, s), 4.30 (1H, q, J=6.6 Hz), 5.6 (1H, br s), 6.8–7.7 (6H, m), 10.68 (1H, s), 11.50 (1H, br s).

$[α]_D^{24.5}$=5° (c=0.1, DMF).

EXAMPLE 44

4-[4-(3-Indolyl)piperidinomethyl]-2-(L-lactoylamino)thiazole mp: 212°–216° C.

$[α]_D^{24.54}$= −5° (c=0.1, DMF).

EXAMPLE 45

4-[4-(3-Indolyl)piperidinomethyl]-2-glycoloylaminothiazole mp: 185°–188° C.

IR (Nujol): 3250, 1680, 1530 cm$^{-1}$.

NMR (DMSO-d$_6$,δ): 1.4–3.4 (9H, m), 3.51 (2H, s), 4.10 (2H, s), 6.8–7.2 (2H, m), 6.96 (1H, s), 7.07 (1H, d, J=2.0 Hz), 7.35 (1H, dd, J=2.0 and 7.0 Hz), 7.58 (1H, dd, J=2.0 and 7.0 Hz), 10.65 (1H, br s).

EXAMPLE 46

4-[4-(3-Indolyl)piperidinomethyl]-2-trifluoroacetylaminothiazole mp: 244°–247° C.

IR (Nujol): 3340, 1594, 1238, 890 cm$^{-1}$.

NMR (DMSO -d$_6$, δ): 1.60–3.8 (10H, m), 4.20 (2H, s), 6.8–7.9 (6H, m), 10.83 (1H, s)

EXAMPLE 47

4-[4-(3-Indolyl)piperidinomethyl]-2-acryloylaminothiazole

IR (Nujol): 3300 (br), 1670, 1630, 1555 cm$^{-1}$.

NMR (DMSO-d$_6$, δ): 1.3–2.4 (4H, m), 2.8–3.1 (2H, m), 3.2–3.4 (3H, m), 3.57 (2H, s), 5.87 (1H, dd, J=8.0 Hz and 4.0 Hz), 6.45 (1H, d, J=4.0 Hz), 6.47 (1H, d, J=8.0 Hz), 6.8–7.15 (2H, m), 7.0 (1H, s), 7.08 (1H, d, J=2.0 Hz), 7.35 (1H, dd, J=7.0 Hz and 2.0 Hz), 7.53 (1H, dd, J=7.0 Hz and 2.0 Hz), 10.7 (1H, br s), 12.3 (1H, br).

EXAMPLE 48

4-[4-(3-Indolyl)piperidinomethyl]-2-crotonoylaminothiazole mp: 115°–118° C.

IR (Nujol): 3250, 1690, 1650, 1550 cm$^{-1}$.

NMR (DMSO-d$_6$, δ): 1.4–2.35 (7H, m), 1.87 (3H, d, J=6.0 Hz), 2.8–3.1 (2H, m), 3.52 (2H, s), 6.16 (1H, dd, J=1.0 Hz and 15.0 Hz), 6.8–7.2 (5H, m), 7.31 (1H, dd, J=8.0 Hz and 2.0 Hz), 7.51 (1H, dd, J=8.0 Hz and 2.0 Hz), 10.69 (1H, br s), 12.10 (1H, br s).

EXAMPLE 49

4-[4-(3-Indolyl)piperidinomethyl]-2-(3-carboxypropionylamino)thiazole mp: 165°–175° C. (dec.).

IR (Nujol): 3150 (br), 2550 (br), 1680, 1550 cm$^{-1}$.

NMR (DMSO-d$_6$, δ): 1.5–2.4 (7H, m), 2.60 (4H, m), 2.8–3.2 (2H, m), 3.55 (2H, s), 6.93 (1H, s), 6.85–7.20 (2H, m), 7.07 (1H, d, J=2.0 Hz), 7.33 (1H, dd, J=3.0 Hz and 7.0 Hz), 7.53 (1H, dd, J=3.0 Hz and 7.0 Hz), 10.73 (1H, br), 12.2 (1H, br).

EXAMPLE 50

4-[4-(3-Indolyl)piperidinomethyl]-2-(3-hydroxypropionylamino)thiazole mp: 212°–218° C. (dec.).

IR (Nujol): 3200, 1650, 1550 cm$^{-1}$.

NMR (DMSO-d$_6$, δ): 1.3–2.3 (6H, m), 2.55 (2H, t, J=6.0 Hz), 2.6–3.1 (3H, m), 3.51 (2H, s), 3.70 (2H, t, J=6.0 Hz), 4.6 (1H, br), 6.90 (1H, s), 7.05 (1H, d, J=2.0 Hz), 6.8–7.1 (2H, m), 7.30 (1H, dd, J=7.0 Hz and 2.0 Hz), 7.49 (1H, dd, J=7.0 Hz and 2.0 Hz), 10.67 (1H, br), 11.9 (1H, br).

EXAMPLE 51

4-[4-(3-Indolyl)piperidinomethyl]-2-(3-morpholinopropionylamino)thiazole dihydrochloride mp: 190°–196° C.

IR (Nujol): 3450, 3150, 2650, 1690, 1545 cm$^{-1}$.

NMR (DMSO-d$_6$, δ): 3.92 (4H, m), 4.32 (2H, br) 6.86–7.16 (2H, m), 7.08 (1H, d, J=2.0 Hz), 7.35 (1H, dd, J=2.0 Hz and 8.0 Hz), 7.59 (1H, s), 7.66 (1H, dd, J=2.0 Hz and 8.0 Hz), 10.9 (1H, br), 10.15 (1H, br), 10.6 (1H, br), 12.54 (1H, br).

EXAMPLE 52

2-Acetylamino-4-[4-(3-indolyl)piperidinomethyl]-thiazole (1.2 g) in a mixture of ethanol (3 ml) and 10% hydrochloric acid (9 ml) was stirred at 80° C. for 2.5 hours. After cooling to ambient temperature, the reaction mixture was concentrated under reduced pressure. To the residue was added dropwise 10% aqueous sodium hydroxide solution (12 ml) under ice-cooling. The resulting crystals were collected, washed with water, dried and recrystallized from ethanol to give 2-amino-4-[4-(3-indolyl)piperidinomethyl]thiazole (410 mg).

mp: 195°-198° C.

IR (Nujol): 3300, 1380, 1330, 1092, 980, 735 cm$^{-1}$.

NMR (DMSO-d$_6$, δ): 1.4-3.4 (1H, m), 6.30 (1H, s), 6.77 (2H, s), 6.8-7.7 (5H, m), 10.7 (1H, s).

Elemental analysis: C$_{17}$H$_{20}$N$_4$S: Calcd.: C 65.35, H 6.45, N 17.93, Found: C 65.46, H 6.42, N 17.55.

The following compounds (Examples 53 and 54) were obtained according to a similar manner to that of Example 52.

EXAMPLE 53

2-Amino-4-[2-[4-(3-indolyl)piperidino]ethyl]thiazole mp: 173.5°-176.0° C. (recrystallized from ethanol).

IR (Nujol): 3425, 3250, 1615, 1505, 1340, 1120, 750 cm$^{-1}$.

NMR (DMSO-d$_6$, δ): 1.3-3.3 (13H, m), 6.15 (1H, s), 6.74 (2H, s), 6.8-7.7 (5H, m), 10.70 (1H, br s).

Mass (m/e): 326 (M+).

Elemental analysis: C$_{18}$H$_{22}$N$_4$S: Calcd.: C 66.23, H 6.79, N 17.16, Found: C 66.03, H 6.67, N 16.79.

EXAMPLE 54

4-[3-[4-(3-Indolyl)piperidino]propyl]-2-aminothiazole mp: 108°-109° C. (recrystallized from 60% ethanol).

IR (Nujol): 3450, 3100, 1635, 1530 cm$^{-1}$.

NMR (DMSO-d$_6$, δ): 1.5-3.0 (15H, m), 6.03 (1H, s), 6.68 (2H, s), 6.9-7.5 (5H, m).

Mass (m/e): 340 (M+).

Elemental analysis: C$_{19}$H$_{24}$N$_4$S·C$_2$H$_5$OH: Calcd.: C 65.25, H 7.82, N 14.49, Found: C 64.90, H 7.56, N 14.40.

EXAMPLE 55

To a mixture of 2-amino-4-[4-(3-indolyl)piperidinomethyl]thiazole (1.73 g), triethylamine (3.1 ml) and N,N-dimethylformamide (15 ml) was added dropwise a solution of mesyl chloride (0.86 ml) in methylene chloride (1 ml) at 5° to 7° C. with stirring. The mixture was further stirred at that temperature for 2 hours, after which a solution of mesyl chloride (0.34 ml) in methylene chloride (0.5 ml) was added. The reaction mixture was further stirred at the same temperature for 1.5 hours. Following addition of water (50 ml), the reaction mixture was extracted with a mixture of chloroform and methanol (60 ml, 10:1 V/V) twice. The extract was washed with a saturated aqueous solution of sodium chloride, dried over magnesium sulfate, and concentrated under reduced pressure. The residue was dissolved in tetrahydrofuran (40 ml) and, then, 10% aqueous sodium hydroxide solution (20 ml) was added gradually thereto. The mixture was stirred at ambient temperature overnight. The reaction mixture was then adjusted to pH 7.0 with diluted hydrochloric acid and extracted with a mixture of chloroform and methanol (100 ml, 10:1 V/V). The organic layer was separated, washed with water, and dried over magnesium sulfate. The solvent was distilled off under reduced pressure and the residue was subjected to column chromatography on silica gel, followed by elution with a mixture of chloroform and methanol (10:1 V/V). The eluate gave 4-[4-(3-indolyl)piperidinomethyl]-2-mesylaminothiazole (480 mg).

mp: 215°-217° C. [recrystallized from chloroform-methanol (20:1 V/V)].

IR (Nujol): 3310, 1380, 1260, 1116, 967, 743 cm$^{-1}$.

Mass: 390 (M+).

NMR (DMSO-d$_6$, δ): 1.5-3.3 (9H, m), 2.80 (3H, s), 3.50 (2H, s), 6.68 (1H, s), 6.8-7.7 (5H, m), 10.72 (1H, s).

Elemental analysis: C$_{18}$H$_{22}$N$_4$O$_2$S$_2$: Calcd.: C 55.36, H 5.68, N 14.35, Found: C 55.13, H 5.48, N 14.03.

EXAMPLE 56

To a mixture of 4-[4-(3-indolyl)piperidinomethyl]-2-aminothiazole (1.5 g), triethylamine (2.68 ml) and N,N-dimethylformamide (15 ml) was added dropwise a solution of propionyl chloride (0.63 ml) in methylene chloride (1.2 ml) over a period of 10 minutes under ice-cooling and the mixture was stirred for 4.5 hours. The reaction mixture was dissolved in a mixture of chloroform and methanol (100 ml, 10:1 V/V) and the solution was washed with water (50 ml×3) and brine (50 ml) successively, and dried over magnesium sulfate. The solvent was evaporated and the residue was subjected to column chromatography on silica gel and the column was eluted with a mixture of chloroform and methanol (30:1 to 15:1 V/V). The fractions containing the desired compound were combined and concentrated to give a residue, which was recrystallized from ethanol to give 4-[4-(3-indolyl)piperidinomethyl]-2-propionylaminothiazole (0.72 g).

mp: 191.5°-195° C.

IR (Nujol): 3380, 1673, 1540, 1180, 738 cm$^{-1}$.

NMR (DMSO-d$_6$, δ): 1.07 (3H, t, J=7.2 Hz), 1.2-3.8 (13H, m), 6.8-7.7 (6H, m), 10.66 (1H, br s), 12.05 (1H, br s).

Mass: 368 (M+).

Elemental analysis: C$_{20}$H$_{24}$N$_4$OS·½C$_2$H$_5$OH: Calcd.: C 64.42, H 6.95, N 14.31, Found: C 64.62, H 6.66, N 14.63.

EXAMPLE 57

To a mixture of 4-[4-(3-indolyl)piperidinomethyl]-2-aminothiazole (3.0 g), triethylamine (5.4 ml) and N,N-dimethylformamide (30 ml) was added dropwise a solution of cyclopropylcarbonyl chloride (2.18 ml) in methylene chloride (2.5 ml) over a period of 30 minutes at 0° C. in a stream of nitrogen gas with stirring. After the reaction was finished, the reaction mixture was filtered and the filtrate was concentrated. The residue was purified by column chromatography on silica gel eluting with a mixture of chloroform and methanol (20:1 V/V) to give 4-[4-(3-indolyl)piperidinomethyl]-2-cyclopropylcarbonylaminothiazole (2.9 g).

mp: 120°-132° C. [recrystallized from ethanol-water (1:1 V/V)].

IR (Nujol): 3560, 3420, 1673, 1550, 1270, 1190, 1000 cm$^{-1}$.

NMR (DMSO-d$_6$, δ): 0.6-1.3 (4H, m), 1.5-3.7 (10H, m), 3.57 (2H, s), 6.8-7.8 (6H, m), 10.90 (1H, s), 12.27 (1H, s).

EXAMPLE 58

To a mixture of 2-amino-4-[2-[4-(3-indolyl)piperidino]ethyl]thiazole (1.24 g) and triethylamine (2.1 ml) in N,N-dimethylformamide (10 ml) was added slowly a solution of mesyl chloride (0.6 ml) in methylene chloride (2 ml) at 0° to 5° C. and the mixture was stirred for 1.5 hours. Mesyl chloride (0.3 ml) was added thereto and the mixture was stirred for 2 hours.

Thereafter, the procedure of Example 55 was followed to give 4-[2-[4-(3-indolyl)piperidino]ethyl]-2-mesylaminothiazole (0.13 g).

mp: 141°–144° C.

IR (Nujol): 1120, 1100, 968, 740 cm$^{-1}$.

NMR (DMSO-d$_6$, δ): 1.5–3.4 (13H, m), 2.80 (3H, s), 6.41 (1H, s), 6.8–7.8 (5H, m), 10.70 (1H, br s).

Mass: 404 (M+).

Elemental analysis: $C_{19}H_{24}N_4O_2S_2 \cdot \frac{1}{4}CHCl_3$: Calcd.: C 53.23, H 5.57, N 12.89, Found: C 52.95, H 5.65, N 12.69.

EXAMPLE 59

To a mixture of 4-[4-(3-indolyl)piperidinomethyl]-2-aminothiazole (2 g), triethylamine (0.98 ml) and N,N-dimethylformamide (20 ml) was added trifluoroacetic anhydride (0.99 ml) over a period of 25 minutes at 1° to 3° C. and the mixture was stirred for 30 minutes. Triethylamine (0.18 ml) and trifluoroacetic anhydride (0.27 ml) was added thereto and the mixture was stirred for 35 minutes. And further, triethylamine (0.27 ml) and trifluoroacetic anhydride (0.27 ml) was added thereto and the mixture was stirred for 1.5 hours. The reaction mixture was concentrated and the residue was purified by column chromatography on silica gel eluting with a mixture of chloroform and methanol (10:1 V/V) to give 4-[4-(3-indolyl)piperidinomethyl]-2-trifluoroacetylaminothiazole (0.46 g).

mp: 244°–247° C. (recrystallized from N,N-dimethylformamide).

IR (Nujol): 3340, 1594, 1238, 890 cm$^{-1}$.

NMR (DMSO-d$_6$, δ): 1.60–3.8 (10H, m), 4.20 (2H, s), 6.8–7.9 (6H, m), 10.83 (1H, s).

Mass (m/e): 408 (M+).

Elemental analysis: $C_{19}H_{19}F_3N_4OS$: Calcd.: C 55.87, H 4.69, N 13.72, Found: C 56.10, H 4.69, N 13.95.

EXAMPLE 60

To a mixture of 4-[4-(3-indolyl)piperidinomethyl]-2-aminothiazole (1 g), triethylamine (1.3 g) and N,N-dimethylformamide (10 ml) was added dropwise a solution of 2-acetoxyacetyl chloride (0.87 g) in methylene chloride (1 ml) in a stream of nitrogen gas with ice-cooling and stirring over a period of 20 minutes. After 3 hours, the reaction mixture was filtered and the residue on the filter paper was washed with N,N-dimethylformamide (10 ml). The filtrate and washings were combined and concentrated under reduced pressure to remove the solvent. The residue was subjected to column chromatography on silica gel and elution was carried out with a mixture of chloroform and methanol (20:1 V/V). The fractions containing the desired compound were collected and concentrated under reduced pressure and the residue was recrystallized from a mixture of water and ethanol to give 4-[4-(3-indolyl)-piperidinomethyl]-2-(2-acetoxyacetylamino)thiazole (0.23 g).

mp: 140°–144° C.

IR (Nujol): 3410, 1750, 1705, 1585 cm$^{-1}$.

NMR (DMSO-d$_6$, δ): 1.5–2.4 (5H, m), 2.13 (3H, s), 2.6–3.9 (4H, m), 3.54 (2H, br s), 4.75 (2H, br s), 6.8–7.2 (2H, m), 7.0 (1H, s), 7.08 (1H, d, J=2.0 Hz), 7.35 (1H, dd, J=2.0 Hz and 7.0 Hz), 7.55 (1H, dd, J=2.0 Hz and 7.0 Hz)

Mass (m/e): 412 (M+),

Elemental analysis: $C_{22}H_{24}N_4O_3S \cdot H_2O$: Calcd.: C 58.58, H 6.09, N 13.01, Found: C 58.71, H 6.21, N 12.90.

EXAMPLE 61

4-[4-(3-Indolyl)piperidinomethyl]-2-aminothiazole (1.5 g) was dissolved in N,N-dimethylformamide (15 ml), and triethylamine (2.69 ml) was added thereto. A solution of 3-methoxycarbonylpropionyl chloride in methylene chloride was added to the mixture at 0° C. with stirring until the starting compound was disappeared. The reaction mixture was filtered and the filtrate was concentrated. The residue was purified by column chromatography on silica gel eluting with a mixture of chloroform and methanol (10:1 V/V) to give 4-[4-(3-indolyl)piperidinomethyl]-2-(3-methoxycarbonylpropionylimino)-3-(3-methoxycarbonylpropionyl)thiazoline (1.35 g).

mp: 171°–173° C. (recrystallized from ethanol-water).

IR (Nujol): 3150, 1745, 1680 cm$^{-1}$.

NMR (DMSO-d$_6$, δ): 1.5–2.4 (6H, m), 2.50 (4H, s), 2.67 (4H, s), 2.7–3.1 (3H, m), 3.54 (2H, s), 3.60 (6H, s), 6.93 (1H, s), 7.08 (1H, d, J=2.0 Hz), 6.9–7.15 (2H, m), 7.33 (1H, dd, J=2.0 Hz and 7.0 Hz), 7.52 (1H, dd, J=2.0 Hz and 7.0 Hz), 10.7 (1H, br).

Elemental analysis: $C_{27}H_{32}N_4O_6S \cdot H_2O$; Calcd.: C 58.05, H 6.13, N 10.03, Found: C 58.16, H 6.02, N 10.15.

To 4-[4-(3-indolyl)piperidinomethyl]-2-(3-methoxycarbonylpropionylimino)-3-(3-methoxycarbonylpropionyl)thiazoline (700 mg) were added ethanol (25 ml) and 1N aqueous solution of sodium hydroxide (3.2 ml) and the mixture was warmed at 50° C. for 6.5 hours. To the reaction mixture was added 1N hydrochloric acid (3.2 ml) and the solvent was evaporated. After the residue was recrystallized from a mixture of ethanol and water, the crystal was collected by filtration and washed with water to give 4-[4-(3-indolyl)-piperidinomethyl]-2-(3-carboxypropionylamino)-thiazole (280 mg).

mp: 165°–175° C. (dec.).

IR (Nujol) : 3150 (br), 2550 (br), 1680, 1550 cm$^{-1}$.

NMR (DMSO-d$_6$, ι): 1.5–2.4 (7H, m), 2.60 (4H, m), 2.8–3.2 (2H, m), 3.55 (2H, s), 6.93 (1H, s), 6.85–7.20 (2H, m), 7.07 (1H, d, J=2.0 Hz), 7.33 (1H, dd, J=3.0 Hz and 7.0 Hz), 7.53 (1H, dd, J=3.0 Hz and 7.0 Hz), 10.73 (1H, br), 12.2 (1H, br).

Mass (m/e): 394 (M+-18), 312.

Elemental analysys: $C_{21}H_{24}N_4O_3S \cdot H_2O$; Calcd.: C 58.58, H 5.62, N 13.01, Found: C 58.32, H 5.87, N 12.91.

The following compounds (Examples 62 to 100) were obtained according to a similar manner to that of Examples 55, 56, 57, 58, 59, 60 or 61.

EXAMPLE 62

4-[4-(3-Indolyl)piperidinomethyl]-2-isobutyrylaminothiazole mp: 183°–187° C.

IR (Nujol): 3280, 3100, 1533, 1100, 758 cm$^{-1}$.

NMR (DMSO-d$_6$, δ): 1.14 (6H, d), 1.2–3.7 (12H, m), 6.8–7.7 (6H, m), 10.70 (1H, br s), 12.05 (1H, br s).

Mass: 382 (M+)

Elemental analysis: $C_{21}H_{26}N_4OS \cdot \frac{1}{2}C_2H_5OH$: Calcd.: C 65.16, H 7.21, N 13.81, Found: C 65.31, H 7.15, N 13.75.

EXAMPLE 63

4-[4-(3-Indolyl)piperidinomethyl]-2-ethylsulfonylaminothiazole mp: 181°–186° C. (recrystallized from ethanol).

IR (Nujol): 3270, 1465, 1110, 1017, 738 cm$^{-1}$.
NMR (DMSO-d$_6$, δ): 1.22 (3H, t, J=7.6 Hz), 1.5–3.7 (11H, m), 3.47 (2H, s), 6.57 (1H, s), 6.9–7.8 (5H, m), 9.46 (1H, br s), 10.78 (1H s).
Mass (m/e): 404 (M+).
Elemental analysis: C$_{19}$H$_{24}$N$_4$O$_2$S$_2$: Calcd.: C 56.41, H 5.98, N 13.85, Found: C 56.13, H 5.93, N 13.52.

EXAMPLE 64

4-[4-(3-Indolyl)piperidinomethyl]-2-isopropylsulfonylaminothiazole and its hydrochloride The following physical data are those of the hydrochloride.

mp: 230°–238° C. (recrystallized from ethanol).
IR (Nujol): 3365, 1540, 1460, 1118, 883, 740 cm$^{-1}$.
NMR (DMSO-d$_6$, δ): 1.24 (6H, d, J=4.2 Hz), 1.8–3.7 (12H, m), 4.27 (2H, s), 6.8–7.0 (6H, m)
Elemental analysis: C$_{20}$H$_{26}$N$_4$O$_2$S$_2$.HCl.7/10EtOH: Calcd.: C 52.75, H 6.45, N 11.50, Found: C 52.52, H 6.17, N 11.81.

EXAMPLE 65

4-[2-[4-(3-Indolyl)piperidino]ethyl]-2-ethylsulfonylaminothiazole and its hydrochloride The following physical data are those of the hydrochloride.

mp: 222°–228° C. (recrystallized from 70% ethanol).
IR (Nujol): 3250, 2650, 1544, 1293, 1117, 890, 743 cm$^{-1}$.
NMR (DMSO-d$_6$, δ): 1.22 (3H, t, J=7.8 Hz), 1.8–4.0 (17H, m), 6.40 (1H, s), 6.7–7.8 (5H, m), 10.75 (1H, br s).
Elemental analysis: C$_{20}$H$_{26}$N$_4$O$_2$S$_2$.HCl: Calcd.: C 52.79, H 5.98, N 12.31, Found: C 52.66, H 5.70, N 12.25.

EXAMPLE 66

4-[3-[4-(3-Indolyl)piperidino]propyl]-2-mesylaminothiazole mp: 210°–214° C. (recrystallized from ethanol-water).
IR (Nujol): 3350, 1535 cm$^{-1}$.
NMR (DMSO-d$_6$, δ): 1.5–3.3 (15H, m), 2.72 (3H, s), 5.80 (1H, br s), 6.25 (1H, s), 6.9–7.5 (5H, m), 10.7 (1H, br s).
Mass (m/e): 418 (M+), 339.
Elemental analysis: C$_{20}$H$_{26}$N$_4$O$_2$S$_2$: Calcd.: C 57.39, H 6.26, N 13.39, Found: C 56.99, H 6.21, N 12.23.

EXAMPLE 67

4-[4-(3-Indolyl)piperidinomethyl]-2-(2-methoxyacetylamino)thiazole and its hydrochloride The following physical data are those of the hydrochloride.

mp: 190°–205° C.
IR (Nujol): 3400, 2650, 2550, 1695, 1550 cm$^{-1}$.
NMR (DMSO-d$_6$, δ): 2.08 (3H, s), 4.20 (2H, s), 4.33 (2H, br s), 1.9–3.8 (9H, m), 6.8–7.8 (6H, m), 10.88 (1H, br s), 12.15 (1H, br s).
Mass (m/e): 384 (M+), 266, 199.
Elemental analysis: C$_{20}$H$_{24}$N$_4$O$_2$S.HCl.⅓CH$_3$COCH$_3$: Calcd.: C 57.28, H 6.18, N 12.72, Found: C 56.75, H 5.96, N 12.45.

EXAMPLE 68

4-[4-(3-Indolyl)piperidinomethyl]-2-acryloylaminothiazole

IR (Nujol): 3300 (br), 1670, 1630, 1555 cm$^{-1}$.
NMR (DMSO-d$_6$, δ): 1.3–2.4 (4H, m), 2.8–3.1 (2H, m), 3.2–3.4 (3H, m), 3.57 (2H, s), 5.87 (1H, dd, J=8.0 Hz and 4.0 Hz), 6.45 (1H, d, J=4.0 Hz), 6.47 (1H, d, J=8.0 Hz), 6.8–7.15 (2H, m), 7.0 (1H, s), 7.08 (1H, d, J=2.0 Hz), 7.35 (1H, dd, J=7.0 Hz and 2.0 Hz), 7.53 (1H, dd, J=7.0 Hz and 2.0 Hz), 10.7 (1H, br s), 12.3 (1H, br).
Mass (m/e): 366 (M+), 199, 167.

EXAMPLE 69

4-[4-(3-Indolyl)piperidinomethyl]-2-crotonoylaminothiazole mp: 115°–118° C.
IR (Nujol): 3250, 1690, 1650, 1550 cm$^{-1}$.
NMR (DMSO-d$_6$, δ): 1.4–2.35 (7H, m), 1.87 (3H, d, J=6.0 Hz), 2.8–3.1 (2H, m), 3.52 (2H, s), 6.16 (1H, dd, J=1.0 Hz and 15.0 Hz), 6.8–7.2 (5H, m), 7.31 (1H, dd, J=8.0 Hz and 2.0 Hz), 7.51 (1H, dd, J=8.0 Hz and 2.0 Hz), 10.69 (1H, br s), 12.10 (1H, br s).
Mass (m/e): 380 (M+), 262, 199.
Elemental analysis: C$_{21}$H$_{24}$N$_4$OS.EtOH: Calcd.: C 64.76, H 7.08, N 13.13, Found: C 64.99, H 6.89, N 13.27.

EXAMPLE 70

2-Acetylamino-4-[4-(3-indolyl)piperidinomethyl]-thiazole mp: 204°–207° C.
IR (Nujol): 3400, 3165, 1686, 1263, 1004, 758, 747 cm$^{-1}$.
NMR (DMSO-d$_6$, δ): 2.32 (3H, s), 1.4–3.2 (9H, m), 3.52 (2H, s), 6.8–7.65 (6H, m), 10.70 (1H, s), 12.08 (1H, s)

EXAMPLE 71

2-Acetylamino-4-[2-[4-(3-indolyl)piperidino]ethyl]-thiazole mp: 203°–204° C.
IR (Nujol): 3275, 1663, 1560, 1305, 1106, 740 cm$^{-1}$.
NMR (DMSO-d$_6$, δ): 2.13 (3H, s), 1.4–3.4 (13H, m), 6.80 (1H, s), 6.8–7.7 (5H, m), 10.79 (1H, s), 12.03 (1H, br s).

EXAMPLE 72

4-[4-(3-Indolyl)piperidinomethyl]-2-pivaloylaminothiazole mp: 93°–96° C.
IR (Nujol): 3235, 1684, 1165, 1148, 1045, 750 cm$^{-1}$.
NMR (CDCl$_3$, δ): 1.33 (9H, s), 1.5–3.4 (9H, m), 3.56 (2H, s), 6.73 (1H, s), 6.9–7.8 (5H, m), 8.10 (1H, br s), 9.00 (1H, br s).

EXAMPLE 73

4-[4-(3-Indolyl)piperidinomethyl]-2-(3-methylureido)-thiazole mp: 222°–224° C. (dec.).
IR (Nujol): 3550, 1715, 1680, 1550 cm$^{-1}$.
NMR (DMSO-d$_6$, δ): 1.5–3.2 (12H, m), 3.50 (2H, br s), 6.50 (1H, m), 6.8–7.2 (2H, m), 7.05 (1H, d, J=2.0 Hz), 7.08 (1H, s), 7.38 (1H, dd, J=2.0 Hz and 7.0 Hz), 7.55 (1H, dd, J=2.0 Hz and 7.0 Hz), 10.7 (1H, br s).

EXAMPLE 74

2-Acetylamino-4-[3-[4-(3-indolyl)piperidino]propyl]-thiazole mp: 168.5°–170° C.
IR (Nujol): 3300, 3100, 1670, 1570, 1300, 985, 750 cm$^{-1}$.
NMR (DMSO-d$_6$, δ): 1.4–3.3 (15H, m), 2.12 (3H, s), 6.70 (1H, s), 6.8–7.7 (5H, m), 10.70 (1H, br s), 12.00 (1H, br s).

EXAMPLE 75

2-Acetylamino-4-[4-(3-indolyl)-1,2,5,6-tetrahydropyridin-1-ylmethyl]thiazole
mp: 217°–219° C.
IR (Nujol): 3150, 1653, 1310, 1125, 750 cm$^{-1}$.
NMR (DMSO-d$_6$, δ): 2.14 (3H, s), 2.4–3.5 (6H, m), 3.64 (2H, s), 6.10 (1H, br s), 6.97 (1H, s), 6.9–8.1 (5H, m), 11.05 (1H, br s), 12.00 (1H, br s).

EXAMPLE 76

4-[4-(3-Indolyl)piperidinomethyl]-2-benzoylaminothiazole
mp: 104°–106° C.
IR (Nujol): 3150, 1670, 1300, 1097, 995, 745, 705 cm$^{-1}$.
NMR (CDCl$_3$, δ): 1.4–3.3 (9H, m), 3.37 (2H, s), 6.78 (2H, s), 6.9–8.4 (12H, m).

EXAMPLE 77

4-[4-(3-Indolyl)piperidinomethyl]-2-(3,3-dimethylbutyrylamino)thiazole
mp: 224.5°–226° C.
IR (Nujol): 3390, 3248, 1650, 1548, 1327, 740 cm$^{-1}$.
NMR (DMSO-d$_6$, δ): 1.03 (9H, s), 2.33 (2H, s), 1.3–3.3 (9H, m), 3.53 (2H, s), 6.95 (1H, s), 7.0–7.8 (5H, m), 10.75 (1H, s), 12.03 (1H, s).

EXAMPLE 78

4-[4-(3-Indolyl)piperidinomethyl]-2-valerylaminothiazole
mp: 142°–144° C.
IR (Nujol): 3240, 1693, 1553, 1105, 745 cm$^{-1}$.
NMR (DMSO-d$_6$, δ): 0.8–3.7 (18H, m), 3.55 (2H, s), 6.92 (1H, s), 6.9–7.7 (5H, m), 10.73 (1H, s), 12.05 (1H, br s).

EXAMPLE 79

4-[4-(3-Indolyl)piperidinomethyl]-2-formylaminothiazole
mp: 217°–221° C.
IR (Nujol): 3460, 1690, 1562, 1280, 852, 755 cm$^{-1}$.
NMR (DMSO-d$_6$, δ): 1.5–3.8 (9H, m), 3.51 (2H, s), 6.8–7.7 (6H, m), 8.45 (1H, s), 10.70 (1H, br s), 12.13 (1H, br s).

EXAMPLE 80

4-[4-(3-Indolyl)piperidinomethyl]-2-butyrylaminothiazole
mp: 163°–165° C.
IR (Nujol): 3200 (broad), 1690, 1555, 745 cm$^{-1}$.
NMR (DMSO-d$_6$, δ): 0.90 (3H, t, J=7.5 Hz), 1.07 (3H, t, J=7.5 Hz), 3.53 (2H, s), 4.33 (1H, br s), 6.92 (1H, s), 6.9–7.7 (5H, m), 10.71 (1H, s), 12.02 (1H, s).

EXAMPLE 81

4-[4-(3-Indolyl)piperidinomethyl]-2-phenylacetylaminothiazole
mp: 190°–191° C.
IR (Nujol): 3250, 1660, 1555, 1545, 735 cm$^{-1}$.
NMR (DMSO-d$_6$, δ): 3.52 (2H, s), 3.74 (2H, s), 6.92 (1H, s), 7.31 (5H, s), 6.9–7.7 (5H, m), 10.71 (1H, s), 12.33 (1H, s)

EXAMPLE 82

4-[4-(5-Methoxy-3-indolyl)piperidinomethyl]-2-acetylaminothiazole
mp: 123°–133° C.
IR (Nujol): 3420, 1690, 1570, 1290, 1220, 810 cm$^{-1}$.
NMR (DMSO-d$_6$, δ): 1.3–2.4 (4H, m), 2.11 (3H, s), 2.5–3.2 (5H, m), 3.34 (2H, s), 3.52 (2H, s), 3.74 (3H, s), 6.70 (1H, dd, J=3 Hz and 9 Hz), 6.90 (1H, s), 6.98 (1H, d, J=3 Hz), 7.03 (1H, d, J=3 Hz), 7.23 (1H, d, J=9 Hz), 10.55 (1H, s), 12.05 (1H, s).

EXAMPLE 83

4-[4-(1-Phenyl-3-indolyl)piperidinomethyl]-2-acetylaminothiazole
mp: 185°–187° C.
IR (Nujol): 3400–3200 (broad), 1690, 1500, 1265, 745 cm$^{-1}$.
NMR (CDCl$_3$, δ): 1.6–3.3 (9H, m), 2.23 (3H, s), 3.59 (2H, s), 6.77 (1H, s), 7.09 (1H, s), 7.45 (5H, s), 7.0–7.8 (4H, m), 10.0 (1H, br s).

EXAMPLE 84

4-[4-(3-Indolyl)piperidinomethyl]-2-ethoxycarbonylaminothiazole
mp: 85° C. (dec.).
IR (Nujol): 3400, 1725, 1563, 1075, 740 cm$^{-1}$.
NMR (DMSO-d$_6$, δ): 1.27 (3H, t, J=6.4 Hz), 1.5–3.5 (9H, m), 3.52 (2H, s), 4.23 (2H, q, J=6.4 Hz), 6.94 (1H, s), 7.0–7.8 (5H, m), 10.75 (1H, s), 11.60 (1H, br s).

EXAMPLE 85

4-[4-(1-Methyl-3-indolyl)piperidinomethyl]-2-acetylaminothiazole
mp: 176°–177° C.
IR (Nujol): 3150, 1690, 1550, 1279, 743 cm$^{-1}$.
NMR (DMSO-d$_6$, δ): 1.5–3.7 (9H, m), 2.16 (3H, s), 3.55 (2H, s), 3.74 (3H, s), 6.8–7.8 (6H, m).

EXAMPLE 86

4-[4-(5-Nitro-3-indolyl)piperidinomethyl]-2-propionylaminothiazole
mp: 222°–224° C.
IR (Nujol): 3290, 1670, 1575, 1520, 1330, 1250, 1100, 735 cm$^{-1}$.
NMR (DMSO-d$_6$, δ): 1.10 (3H, t, J=7.5 Hz), 2.40 (2H, q, J=7.5 Hz), 1.4–3.5 (9H, m), 3.50 (2H, s), 6.85 (1H, s), 7.3–8.5 (4H, m), 11.48 (1H, br s), 11.91 (1H, br s).

EXAMPLE 87

4-[4-(3-Indolyl)piperidinomethyl]-2-[(2R)-2acetoxypropionylamino]thiazole
IR (Nujol): 3430, 1744, 1692, 1550, 1463 cm$^{-1}$.
NMR (CDCl$_3$, δ): 1.55 (3H, d, J=6.9 Hz), 1.6–3.3 (9H, m), 2.17 (3H, s), 3.55 (2H, s), 5.38 (1H, q, J=6.9 Hz), 6.8–8.1 (8H, m).
[α]$_D^{24.5}$=12.0° (c=0.1, DMF).

EXAMPLE 88

4-[4-(3-Indolyl)piperidinomethyl]-2-[(2S)-2acetoxypropionylamino]thiazole
IR (Nujol): 3430, 1744, 1692, 1550, 1463 cm$^{-1}$.

EXAMPLE 89

4-[4-(5-Amino-3-indolyl)piperidinomethyl]-2-propionylaminothiazole
mp: 115°–118° C. (dec.).
IR (Nujol): 3400, 3300, 3200, 1685, 1555, 1350, 1330, 1275, 1200 cm$^{-1}$.
NMR (DMSO-d$_6$, δ): 1.05 (3H, t, J=7.0 Hz), 2.41 (2H, q, J=7.0 Hz), 1.3–3.6 (9H, m), 3.50 (2H, s), 4.30

(2H, br s), 6.3–7.0 (5H, m), 10.10 (1H, br s), 11.88 (1H, br s).

EXAMPLE 90

4-[4-(5-Acetylamino-3-indolyl)piperidinomethyl]-2-propionylaminothiazole
mp: 263°–267° C.
IR (Nujol): 3370, 1680, 1650, 1590, 1560 cm$^{-1}$.
NMR (DMSO-d$_6$, δ): 1.08 (3H, d, J=9.0 Hz), 2.0 (3H, s), 2.35 (2H, q, J=9.0 Hz), 1.4–3.2 (9H, m), 3.48 (2H, s), 6.8–9.56 (5H, m), 10.55 (1H, br s), 11.93 (1H, br s).

EXAMPLE 91

4-[4-(3-Indolyl)piperidinomethyl]-2-(D-lactoylamino)-thiazole
mp: 213°–216.5° C.
IR (Nujol): 3360, 3190, 1663, 1570, 1138 cm$^{-1}$. NMR (DMSO-d$_6$, δ): 1.27 (3H, d, J=6.6 Hz), 1.4–3.6 (9H, m), 3.52 (2H, s), 4.30 (1H, q, J=6.6 Hz), 5.6 (1H, br s), 6.8–7.7 (6H, m), 10.68 (1H, s), 11.50 (1H, br s).
$[\alpha]_D^{24.5}$ = 5° (c=0.1, DMF).

EXAMPLE 92

4-[4-(3-Indolyl)piperidinomethyl]-2-(L-lactoylamino)-thiazole
mp: 212°–216° C.
$[\alpha]_D^{24.5}$ = −5°(c=0.1, DMF).

EXAMPLE 93

4-[4-(3-Indolyl)piperidinomethyl]-2-glycoloylamino-thiazole
mp: 185°–188° C.
IR (Nujol): 3250, 1680, 1530 cm$^{-1}$.
NMR (DMSO-d$_6$, δ): 1.4–3.4 (9H, m), 3.51 (2H, s), 4.10 (2H, s), 6.8–7.2 (2H, m), 6.96 (1H, s), 7.07 (1H, d, J=2.0 Hz), 7.35 (1H, dd, J=2.0 Hz and 7.0 Hz), 7.58 (1H, dd, J=2.0 Hz and 7.0 Hz), 10.65 (1H, br s).

EXAMPLE 94

4-[4-(3-Indolyl)piperidinomethyl]-2-(3-methoxypropionylamino)thiazole
mp: 157°–158° C.
IR (Nujol): 3200, 1696, 1554, 1106, 740 cm$^{-1}$.
NMR (DMSO-d$_6$, δ): 1.5–3.5 (9H, m), 2.65 (2H, t, J=6.0 Hz), 3.23 (3H, s), 3.52 (2H, s), 3.63 (2H, t, J=6.0 Hz), 6.8–7.6 (6H, m), 10.7 (1H, s), 12.06 (1H, s).

EXAMPLE 95

4-[4-(3-Indolyl)piperidinomethyl]-2-(3-aetoxy propionylamino)thiazole
mp: 73°–75° C.
IR (Nujol): 3610, 3430, 1714, 1680, 1565 cm$^{-1}$.
NMR (DMSO-d$_6$, δ): 1.5–2.4 (6H, m), 2.0 (3H, s), 2.76 (2H, t, J=6.0 Hz), 2.6–3.25 (3H, m), 3.54 (2H, s), 4.28 (2H, t, J=6.0 Hz), 6.95 (1H, s), 7.06 (1H, J=2.0 Hz), 6.8–7.15 (2H, m), 7.33 (1H, dd, J=2.0 Hz and 7.0 Hz), 7.51 (1H, dd, J=2.0 Hz and 7.0 Hz), 10.71 (1H, br), 12.17 (1H, br).

EXAMPLE 96

4-[4-(3-Indolyl)piperidinomethyl]-2-(3-methoxycarbonylpropionylamino)thiazole
mp: 101°–107° C.
IR (Nujol): 3410, 1735, 1695, 1585 cm$^{-1}$.
NMR (DMSO-d$_6$, δ): 1.4–2.4 (7H, m), 2.8–3.15 (2H, m), 2.69 (4H, s), 3.54 (2H, s), 3.62 (3H, s), 6.93 (1H, s), 6.8–7.2 (2H, m), 7.07 (1H, d, J=2.0 Hz), 7.34 (1H, dd, J=2.0 hz and 7.0 Hz), 7.53 (1H, dd, J=2.0 Hz and 7.0 Hz), 10.71 (1H, br), 12.1 (1H, br).

EXAMPLE 97

4-[4-(3-Indolyl)piperidinomethyl]-2-(N-methyl-N-propionylamino)thiazole
mp: 167°–167.5° C.
IR (Nujol): 3150, 1670, 1490, 1123, 735 cm$^{-1}$.
NMR (DMSO-d$_6$, δ): 1.10 (3H, t, J=7.5 Hz), 1.4–3.4 (9H, m), 2.69 (2H, q, J=7.5 Hz), 3.56 (2H, s), 3.63 (3H, s), 6.8–7.7 (6H, m), 10.70 (1H, s).

EXAMPLE 98

4-[4-(3-Indolyl)piperidinomethyl]-2-acetylamino-5-chlorothiazole
mp: 145° C. (dec.).
IR (Nujol): 3440, 1685, 1574, 1300, 740 cm$^{-1}$.
NMR (DMSO-d$_6$, δ): 1.3–3.6 (9H, m), 2.13 (3H, s), 3.55 (2H, s), 6.8–7.7 (5H, m), 10.77 (1H, s).

EXAMPLE 99

4-[4-(3-Indolyl)piperidinomethyl]-2-(3-hydroxypropionylamino)thiazole
mp: 212°–218° C. (dec.).
IR (Nujol): 3200, 1650, 1550 cm$^{-1}$.
NMR (DMSO-d$_6$, δ): 1.3–2.3 (6H, m), 2.55 (2H, t, J=6.0 Hz), 2.6–3.1 (3H, m), 3.51 (2H, s), 3.70 (2H, t, J=6.0 Hz), 4.6 (1H, br), 6.90 (1H, s), 7.05 (1H, d, J=2.0 Hz), 6.8–7.1 (2H, m), 7.30 (1H, dd, J=7.0 Hz and 2.0 Hz), 7.49 (1H, dd, J=7.0 Hz and 2.0 Hz), 10.67 (1H, br), 11.9 (1H, br).

EXAMPLE 100

4-[4-(3-Indolyl)piperidinomethyl]-2-(3-morpholinopropionylamino)thiazole dihydrochloride
mp: 190°–196° C.
IR (Nujol): 3450, 3150, 2650, 1690, 1545 cm$^{-1}$.
NMR (DMSO-d$_6$, δ): 3.92 (4H, m), 4.32 (2H, br), 6.86–7.16 (2H, m), 7.08 (1H, d, J=2.0 Hz), 7.35 (1H, dd, J=2.0 Hz, and 8.0 Hz), 7.59 (1H, s), 7.66 (1H, dd, J=2.0 Hz and 8.0 Hz), 10.9 (1H, br), 10.15 (1H, br), 10.6 (1H, br), 12.54 (1H, br).

EXAMPLE 101

A mixture of 4-[4-(5-nitro-3-indolyl)piperidinomethyl]-2-propionylaminothiazole (1.39 g) and ethanol (60 ml) was added to a solution of ammonium chloride (1.08 g) in water (20 ml), followed by stirring at 80° C. Iron (1.13 g) was added thereto and the mixture was refluxed for 2 hours, after which it was filtered. The residue was washed with hot ethanol and the filtrate and washings were combined and concentrated under reduced pressure. The residue was made alkaline to litmus paper with 2N aqueous sodium hydroxide solution and extracted with ethyl acetate. The extract was washed with a saturated aqueous solution of sodium chloride, dried over magnesium sulfate, and concentrated under reduced pressure. The residue was subjected to column chromatography on silica gel and elution was carried out with a mixture of chloroform and methanol to give 4-[4-(5-amino-3-indolyl)piperidinomethyl]-2-propionylaminothiazole (0.92 g).
mp: 115°–118° C. (dec.) (recrystallized from ethanol).
IR (Nujol): 3400, 3300, 3200, 1685, 1555, 1350, 1330, 1275, 1200 cm$^{-1}$.
NMR (DMSO-d$_6$, δ): 1.05 (3H, t, J=7.0 Hz), 2.41 (2H, q, J=7.0 Hz), 1.3–3.6 (9H, m), 3.50 (2H, s), 4.30

(2H, br s), 6.3–7.0 (5H, m), 10.10 (1H, br s), 11.88 (1H, br s).
Mass (m/e): 383 (M+).
Elemental analysis: $C_{20}H_{25}N_5OS \cdot C_2H_5OH$: Calcd.: C 61.51, H 7.27, N 16.30, Found: C 61.63, H 6.86, N 15.98.

EXAMPLE 102

To a solution of 4-[4-(5-amino-3-indolyl)-piperidinomethyl]-2-propionylaminothiazole (0.5 g) in pyridine (5 ml) was grandually added acetic anhydride (0.16 ml) with stirring and ice-cooling. After 2.5 hours of stirring, the reaction mixture was poured into ice-water and extracted with a mixture of choloroform and methanol (10:1 V/V). The extract was washed with a saturated aqueous solution of sodium chloride, dried over anhydrous magnesium sulfate and concentrated under reduced pressure. The residue was subjected to column chromatography on silica gel and elution was carried out with a mixture of chloroform and methanol to give 4-[4-(5-acetylamino-3-indolyl)piperidino]-2-propionylaminothiazole (0.27 g).

mp: 263°–267° C. (recrystallized form ethanol-water).
IR (Nujol): 3370, 1680, 1650, 1590, 1560 cm$^{-1}$.
NMR (DMSO-d$_6$, δ): 1.08 (3H, d, J=9.0 Hz), 2.0 (3H, s), 2.35 (2H, q, J=9.0 Hz), 1.4–3.2 (9H, m), 3.48 (2H, s), 6.8–9.56 (5H, mm), 10.55 (1H, br s), 11.93 (1H, br s).
Mass (m/e): 425 (M+).
Elemental analysis: $C_{22}H_{27}N_5O_2S$. Calcd.: C 62.09, H 6.39, N 16.46, Found: C 61.98, H 6.23, N 16.16.

EXAMPLE 103

In ethanol (5 ml) was dissolved 4-[4-(3-indolyl)-piperidinomethyl]-2-[(2R)-2-acetoxypropionylamino]-thiazole (1 g) and under ice-cooling, 1N aqueous sodium hydroxide solution (2.34 ml) was added. The mixture was stirred for 1 hour at the same temperature and, then, for 1.5 hours at ambient temperature. Thereafter, 1N aqueous sodium hydroxide solution (0.7 ml) was further added and the mixture was stirred at ambient temperature for another 2 hours. The reaction mixture was then neutralized with 1N hydrochloric acid and concentrated under reduced pressure. The residue was extracted with a mixture of chloroform and methanol (10:1 V/V) and the extract was washed with a saturated aqueous solution of sodium chloride, dried over magnesium sulfate, and concentrated under reduced pressure. The residue was subjected to column chromatography on silica gel and elution was carried out with a mixture of chloroform and methanol (10:1 V/V) to give 4-[4-(3-indolyl)piperidinomethyl]-2-(D-lactoylamino)thiazole (0.39 g).

mp: 213°–216.5° C. (recrystallized from ethyl acetate).
IR (Nujol): 3360, 3190, 1663, 1570, 1138 cm$^{-1}$. NMR (DMSO-d$_6$, δ): 1.27 (3H, d, J=6.6 Hz), 1.4–3.6 (9H, m), 3.52 (2H, s), 4.30 (1H, q, J=6.6 Hz), 5.6 (1H, br s), 6.8–7.7 (6H, m), 10.68 (1H, s), 11.50 (1H, br s).
$[\alpha]_D^{24.5} = 5°$ (c=0.1, DMF).
Mass (m/e): 384 (M+).
Elemental analysis: $C_{20}H_{24}N_4O_2S$. Calcd.: C 62.48, H 6.29, N 14.57, Found: C 62.80, H 6.22, N 14.48.

EXAMPLE 104

4-[4-(3-Indolyl)piperidinomethyl]-2-(L-lactoylamino)-thiazole was obtained according to a similar manner to that of Example 103.
mp: 212°–216° C. (recrystallized from ethyl acetate).
$[\alpha]_D^{24.5} = -5°$ (c=0.1, DMF).

EXAMPLE 105

To a suspension of 4-[4-(3-indolyl)piperidinomethyl]-2-(2-acetoxyacetylamino)thiazole (0.9 g) in ethanol (20 ml) was added 1N aqueous solution of sodium hydroxide (3 ml). After one hour of stirring, the reaction mixture was concentrated and the resulting precipitate was collected by filtration and recrystallized from a mixture of water and ethanol to give 4-[4-(3-indolyl)-piperidinomethyl]-2-glycoloylaminothiazole (0.28 g).
mp: 185°–188° C.
IR (Nujol): 3250, 1680, 1530 cm$^{-1}$.
NMR (DMSO-d$_6$, δ): 1.4–3.4 (9H, m), 3.51 (2H, s), 4.10 (2H, s), 6.8–7.2 (2H, m), 6.96 (1H, s), 7.07 (1H, d, J=2.0 Hz), 7.35 (1H, dd, J=2.0 Hz and 7.0 Hz), 7.58 (1H, dd, J=2.0 Hz and 7.0 Hz), 10.65 (1H, br s).
Mass (m/e): 370 (M+).
Elemental analysis: $C_{19}H_{22}N_4O_2S$. Calcd.: C 60.86, H 6.05, N 14.94, Found: C 60.56, H 5.90, N 14.59.

EXAMPLE 106

To 4-[4-(3-indolyl)piperidinomethyl]-2-(3acetoxypropionylamino)thiazole (1.1 g) were added ethanol (20 ml) and 1N aqueous solution of sodium hydroxide (2.6 ml) and the mixture was stirred at an ambient temperature for 3.5 hours. 1N hydrochloric acid (2.6 ml) was added thereto and ethanol was evaporated. The residue was extracted with a mixture of chloroform and methanol (10:1 V/V) and the extract was dried over magnesium sulfate and concentrated. The residue was purified by column chromatography on silica gel eluting with a mixture of chloroform and methanol (10:1 V/V) to give 4-[4-(3-indolyl)piperidinomethyl]-2(3-hydroxypropionylamino)thiazole (290 mg).
mp: 212°–218° C. (dec.) (recrystallized from ethanol-water).
IR (Nujol): 3200, 1650, 1550 cm$^{-1}$.
NMR (DMSO-d$_6$, δ): 1.3–2.3 (6H, m), 2.55 (2H, t, J=6.0 Hz), 2.6–3.1 (3H, m), 3.51 (2H, s), 3.70 (2H, t, J=6.0 Hz), 4.6 (1H, br), 6.90 (1H, s), 7.05 (1H, d, J=2.0 Hz), 6.8–7.1 (2H, m), 7.30 (1H, dd, J=7.0 Hz and 2.0 Hz), 7.49 (1H, dd, J=7.0 Hz and 2.0 Hz), 10.67 (1H, br), 11.9 (1H, br).
Mass (m/e): 384 (M+), 366, 266, 199.
Elemental analysis: $C_{20}H_{24}N_4O_2S$: Calcd.: C 62.48, H 6.29, N 14.57, Found: C 62.79, H 6.33, N 14.68.

EXAMPLE 107

A mixture of 4-[4-(3-indolyl)piperidinomethyl]-2-acryloylaminothiazole (360 mg) and morpholine (870 mg) was heated at 105° C. After the reaction finished, excess morpholine was distilled off, and the residue was purified by column chromatography on silica gel eluting with a mixture of chloroform and methanol (20:1 V/V) to give 4-[4-(3-indolyl)piperidinomethyl]2-(3-morpholinopropionylamino)thiazole, which was treated with an ethanol solution of hydrogen chloride to give dihydrochloride thereof.
mp: 190°–196° C. (recrystallized from acetonee-thanol)
IR (Nujol): 3450, 3150, 2650, 1690, 1545 cm$^{-1}$.
NMR (DMSO-d$_6$, δ): 3.92 (4H, m), 4.32 (2H, br), 6.86–7.16 (2H, m), 7.08 (1H, d, J=2.0 Hz), 7.35 (1H, dd, J=2.0 Hz and 8.0 Hz), 7.59 (1H, s), 7.66 (1H, dd, J=2.0 Hz and 8.0 Hz), 10.9 (1H, br), 10.15 (1H, br), 10.6 (1H, br), 12.54 (1H, br).
Mass (m/e): 453 (M+), 366, 199, 56.

EXAMPLE 108

In hot ethanol (80 ml) was dissolved 4-[2-[4-(3-indolyl)piperidino]ethyl]-2-mesylaminothiazole (0.5 g). After the solution was cooled to ambient temperature, 15% solution of hydrogen chloride in ethanol (3 ml) was added, followed by cooling to 5° C. The resulting precipitate was collected by filtration and washed with ethanol. This precipitate was recrystallized from water (50 ml) to give 4-[2-[4-(3-indolyl)piperidino]ethyl]-2-mesylaminothiazole hydrochloride (0.42 g).

mp: 200°–230° C. (dec.),

IR (Nujol): 3450, 1525, 1280, 1130, 970, 900, 760 cm$^{-1}$.

Elemental analysis: $C_{19}H_{24}N_4O_2S_2 \cdot HCl$: Calcd.: C 51.75, H 5.71, N 12.70, Found: C 51.76, H 5.43, N 12.67.

What we claim is:

1. A thiazole compound of the formula:

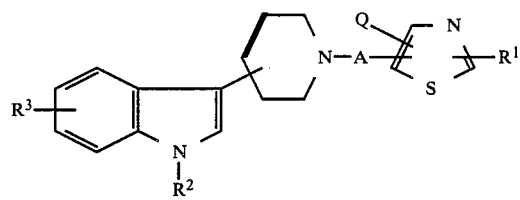

wherein $R^1$ is amino, lower alkylamino, lower alkenylamino, lower alkynylamino, lower alkanoylamino, higher alkanoylamino, lower alkenoylamino, lower alkynoylamino, mono- or di- or trihalo(lower)alkanoylamino, cyclo(lower)alkylcarbonylamino, cyclo(lower)alkenylcarbonylamino, loweralkoxycarbonylamino, hydroxy(lower)alkanoylamino, lower alkoxy(lower) alkanoylamino, lower alkanoyloxy(lower)alkanoylamino, ureido, lower alkylureido, amino-substituted alkanoylamino, carboxy substituted lower alkanoylamino, lower alkoxycarbonylcarbonylamino, lower alkoxycarbonyl(lower)alkanoylamino, lower alkanoylcarbonylamino, lower alkanoyl(lower)alkanoylamino, amino- and carboxy-substituted alkanoylamino, benzoylamino, nicotinoylamino, phenylalkanoylamino, phenylalkenoylamino, morpholino(lower)alkanoylamino, lower alkylsulfonylamino, tosylamino, phenylsulfonylamino, phenylamino, N,N-di(lower)alkylsulfonylamino, N-(lower)alkanoyl-N-(lower)alkylamino, N-cyclo(lower)alkylcarbonyl-N-(lower)alkylamino or N-(lower)alkylsulfonyl-N-(lower)alkylamino, $R^2$ is hydrogen, lower alkyl or phenyl, $R^3$ is hydrogen, nitro, amino, lower alkanoylamino, hydroxy or lower alkoxy, A is lower alkylene, Q is hydrogen or halogen, and a heavy solid line means a single or double bond, or a pharmaceutically acceptable salt thereof.

2. A compound of claim 1, wherein a heavy solid line means a single bond.

3. A compound of claim 2, wherein a compound is the formula:

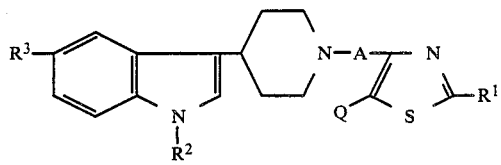

4. A compound of claim 3, wherein $R^1$ is lower alkanoylamino, lower alkenoylamino, mono- or di- or tri-halo(lower)alkanoylamino, cyclo(lower)alkylcarbonylamino, lower alkoxycarbonylamino, hydroxy(lower)alkanoylamino, lower alkoxy(lower)alkanoylamino, lower alkanoyloxy(lower) alkanoylamino, lower alkylureido, carboxy substituted lower alkanoylamino, lower alkoxycarbonyl(lower)alkaonylamino, benzoylamino, phenylalkanoylamino, morpholino (lower)alkanoylamino, or lower alkylsulfonylamino.

5. A compound of claim 4,
wherein $R^1$ is lower alkanoylamino, cyclo(lower)alkylcarbonylamino, or lower alkylsulfonylamino,
$R^2$ is hydrogen,
$R^3$ is hydrogen, and
Q is hydrogen.

6. A compound of claim 5, wherein $R^1$ is lower alkanoylamino.

7. A compound of claim 6, which is 4-[4-(3-indolyl)-piperidinomethyl]-2-propionylaminothiazole.

8. A compound of claim 5, wherein $R^1$ is cyclo(lower)alkylcarbonylamino.

9. A compound of claim 8, which is 4-[4-(3-indolyl)-piperidinomethyl]-2-cyclopropylcarbonylaminothiazole.

10. A compound of claim 5, wherein $R^1$ is lower alkylsulfonylamino.

11. A compound of claim 10, which is 4-[2-[4-(3-indolyl)piperidino]ethyl]-2-mesylaminothiazole.

12. A compound of claim 10, which is 4-[4-(3-indolyl)piperidinomethyl]-2-mesylaminothiazole.

13. An antiallergic pharmaceutical composition comprising an antialleigically effecitve amount of a compound of claim 1, an active ingredient, in association with a pharmaceutically acceptable, substantially nontoxic carrier or excipient.

14. A method for the therapeutic treatment of allergic disease which comprises administering an antiallergically effective amount of a compound of claim 1 in human beings or animals.

* * * * *